(12) United States Patent
Arelekatti et al.

(10) Patent No.: US 11,497,627 B2
(45) Date of Patent: Nov. 15, 2022

(54) LOCKING AND DAMPING MECHANISM FOR A PROSTHETIC KNEE JOINT

(71) Applicant: Massachusetts Institute of Technology, Cambridge, MA (US)

(72) Inventors: Venkata N. M. Arelekatti, Cambridge, MA (US); Amos G. Winter, V, Somerville, MA (US); Jason Z. Fischman, Wesley Hills, NY (US); Athena Yeh Huang, Cambridge, MA (US); Youngjun Joh, Cambridge, MA (US)

(73) Assignee: MASSACHUSETTS NSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/617,836

(22) PCT Filed: Jun. 1, 2018

(86) PCT No.: PCT/US2018/035608
§ 371 (c)(1),
(2) Date: Nov. 27, 2019

(87) PCT Pub. No.: WO2018/222997
PCT Pub. Date: Dec. 6, 2018

(65) Prior Publication Data
US 2020/0188138 A1 Jun. 18, 2020

Related U.S. Application Data

(60) Provisional application No. 62/514,066, filed on Jun. 2, 2017.

(51) Int. Cl.
*A61F 2/64* (2006.01)
*A61F 2/50* (2006.01)
*A61F 2/68* (2006.01)

(52) U.S. Cl.
CPC ...... *A61F 2/644* (2013.01); *A61F 2002/5006* (2013.01); *A61F 2002/6854* (2013.01)

(58) Field of Classification Search
CPC .............. A61F 2/644; A61F 2002/5006; A61F 2002/6854; A61F 2/64
See application file for complete search history.

(56) References Cited

U.S. PATENT DOCUMENTS

| 688,936 A | 12/1901 | Devol |
|---|---|---|
| 2,943,622 A | 7/1960 | Nelson |

(Continued)

FOREIGN PATENT DOCUMENTS

| EP | 1 186 279 | 3/2002 |
|---|---|---|
| WO | WO 2008/064462 | 6/2008 |

(Continued)

OTHER PUBLICATIONS

European Patent Office, International Search Report and Written Opinion dated Oct. 16, 2018 for PCT Application No. PCT/US2018/035608; 19 pages.

(Continued)

*Primary Examiner* — Jacqueline Woznicki
*Assistant Examiner* — Mihret Tafesse
(74) *Attorney, Agent, or Firm* — Hamilton, Brook, Smith & Reynolds, P.C.

(57) ABSTRACT

A high performance, low-cost passive prosthetic knee includes one or more modules to enable able-bodied gait by transfemoral amputees to improve metabolic efficiency and reduce stigma from conspicuous abnormal gaits. A stance stability module includes a latch with a virtual lock axis that automatically locks and unlocks. An early stance flexion module enables able-bodied gait during stance. Hydraulic fluid dampers ensure reliable swing phase control. A swing extension energy storage module stores and returns energy (Continued)

as the knee locks and unlocks, respectively. These modules may be used together, in any combination, or individually.

20 Claims, 24 Drawing Sheets

(56) References Cited

U.S. PATENT DOCUMENTS

| | | | |
|---|---|---|---|
| 5,545,232 | A | 8/1996 | Van de Veen |
| 5,645,590 | A | 7/1997 | Van de Veen |
| 7,087,090 | B2 | 8/2006 | Andrysek et al. |
| 7,909,885 | B2 | 3/2011 | Andrysek |
| 7,918,898 | B2 | 4/2011 | Andrysek |
| 10,405,997 | B2 | 9/2019 | Arelekatti et al. |
| 2005/0149203 | A1* | 7/2005 | Andrysek ............... A61F 2/644 623/44 |
| 2005/0203639 | A1* | 9/2005 | Wild ...................... A61F 2/644 623/44 |
| 2014/0039642 | A1* | 2/2014 | Nijiman .................. A61F 2/66 623/33 |

FOREIGN PATENT DOCUMENTS

| | | |
|---|---|---|
| WO | WO 2012/166853 | 12/2012 |
| WO | WO 2016/179281 | 11/2016 |

OTHER PUBLICATIONS

European Patent Office, International Search Report and Written Opinion dated Jul. 20, 2016 for PCT Application No. PCT/US2016/030779; 11 pages.
International Bureau of WIPO, International Preliminary Report on Patentability for PCT Application No. PCT/US2016/030779 dated Nov. 7, 2017; 8 pages.
"Guidelines for Training Personnel in Developing Countries for Prosthetics and Orthotics Services," World Health Org., 2005 (57 pages).
"World Report on Disability," World Health Org., 2011 (350 pages).
"Orthotics and Prosthetics", *Journal of the American Orthotic and Prosthetic Association*, vol. 40, No. 1 Spring 1986 (74 pages).
Andrysek, J., "LC Knee™," at least as early as May 4, 2016 (2 pages).
Andrysek, J., "Lower-limb prosthetic technologies in the developing world: A review of literature from 1994-2010," *Prosthet. Orthot. Int.*, vol. 34, No. 4, pp. 378-398 (2010).
Andrysek, et al., "Mobility Function of a Prosthetic Knee Joint with an Automatic Stance Phase Lock", *Prosthet. Orthot. Int.*, vol. 35, No. 2, pp. 163-170 (2011).
Arelekatti, V.N.M., et al., "Design of Mechanism and Preliminary Field Validation of Low-Cost, Passive Prosthetic Knee for Users with Transfemoral Amputation in India", vol. 5A: 39$^{th}$ Mechanism and Robotics Conference, Aug. 2, 2015, pp. 1-8.
Arelekatti, V.N.M., et al., "Design and Preliminary Field Validation of a Fully Passive Prosthetic Knee Mechanism for Users with Transfemoral Amputation in India," *ASME J. Mech. & Robotics*, Feb. 5, 2018 (23 pages).
Arelekatti, V.N.M., et al., "Draft: Design of a Passive Prosthetic Knee Mechanism for Users With Transfemoral Amputation in India," Proc. ASME 2016 Inter'l Design Eng. Tech. Conf., Aug. 21-24, 2016, Charlotte, US (9 pages).
Arelekatti, V.N.M., et al., "Design of a Fully Passive Prosthetic Knee Mechanism for Transfemoral Amputees in India", *IEEE Int'l Conf. Rehab. Robotics*, 350-356 (2015).
Blumentritt Siegmar, et al., "Design Principles, Biomechanical Data and Clinical Experience With a Polycentric Knee Offering Controlled Stance Phase Knee Flexion: A Preliminary Report," *J. of Prosthetics and Orthotics*, vol. 9, No. 1, p. 18 (1997).
Cummings, D., "Prosthetics in the developing world: a review of the literature," *Prosthet. Orthot. Int.*, vol. 20, No. 1, pp. 51-60 (1996).
Hammer, S. et al., "Designing for Scale: Development of the ReMotion Knee for Global Emerging Markets," *Ann. Biomed. Eng.*, vol. 41, No. 9, pp. 1851-1859 (2013).
Horgan, et al., "Psychosocial Adjustment to Lower-limb Amputation: A Review", *Disability and Rehabilitation*, vol. 26, No. 14/15, pp. 837-850 (2004).
Narang, Y.S. and Winter, A.G., "Effects of prosthesis mass on hip energetics, prosthetic knee torque, and prosthetic knee stiffness and damping parameters required for transfemoral amputees to walk with normative kinematics," In ASME 2014 International Design Engineering Technical Conferences and Computers and Information in Engineering Conference, vol. 5A: 38th Mechanisms and Robotics IDETC Conference, Aug. 2014. (8 pages).
Narang, Y., "Identification of Design Requirements for a High-Performance, Low-Cost, Passive Prosthetic Knee Through User Analysis and Dynamic Simulation," M.S. thesis, Dept. Mech. Eng., MIT, Cambridge, MA, Jun. 2013, (98 pages).
Narang, I.C., et al., "Functional capabilities of lower limb amputees", *Prosthetics and Orthotics International*, vol. 8, pp. 43-51(1984).
Narang, et al., "The Effects of Prosthesis Inertial Properties on Prosthetic Knee Moment and Hip Energetics Required to Achieve Able-Bodied Kinematics", *IEEE Transations on Neural Systems and Rehabilitation Engineering*, vol. 24, No. 7, Jul. 2016, pp. 754-763.
Narang, et al., "The Effects of the Inertial Properties of Above-Knee Prostheses on Optimal Stiffness, Damping, and Engagement Parameters of Passive Prosthetic Knees", *Journal of Biomechanical Engineering*, vol. 138, Dec. 2016, pp. 121002-1-121002-10.
Rybarczyk, et al., "Body Image, Perceived Social Stigma, and the Prediction of Psychological Adjustment to Leg Amputation", *Rehabilitation Psychology*, vol. 40, No. 2, 1995, pp. 95-110.
Sharp, Madeleine, "The Jaipur Limb and Foot", *Medicine Conflict and Survival*, 10:3, 1994, pp. 207-211.
Wyss, Dominik, "Evaluation and Design of a Globally Applicable Rear-Locking Prosthetic Knee Mechanism", Thesis for Master of Applied Science, Graduate Dept. of Mechanical & Industrial Engineering, University of Toronto, 2012, (135 pages).
Wyss, D., et al., "Priorities in lower limb prosthetic service delivery based on an international survey of prosthetists in low- and high-income countries", *Prosthet. Orthot. Int.*, vol. 39, No. 2, pp. 102-111 (2015).
Yang, et al., Floor Reaction Orthosis: Clinical Experience, *Orthotics and Prosthetics*, vol. 40, No. 1, pp. 33-37 (1986).

* cited by examiner

LOCKING AND DAMPING MECHANISM FOR A PROSTHETIC KNEE JOINT

CROSS REFERENCE TO RELATED APPLICATIONS

This application is a national phase entry of international patent application no. PCT/US2018/035608, which claims the benefit of U.S. Provisional Patent Application No. 62/514,066, filed Jun. 2, 2017, titled "Locking and Damping Mechanism for a Prosthetic Knee Joint," the entire contents of each of which are hereby incorporated by reference herein, for all purposes.

BACKGROUND

Technical Field

The present invention relates to prosthetic knee joints and, more particularly, to passive prosthetic knee joints that include stance stability modules, early stance flexion modules, swing phase control modules and/or swing extension energy storage modules.

Related Art

There is a significant need for low-cost, high-performance prosthetic knee technology for transfemoral amputees, particularly in certain countries, such as India. Replicating able-bodied gait in amputees is biomechanically necessary to reduce metabolic cost, and it is equally important to mitigate socio-economic discrimination faced by amputees in developing countries due to their conspicuous gait deviations.

It is estimated that about 200,000 above-knee amputees live in India and that 47% of amputees experience change or loss of employment following the amputation [Refs. 6-8]. Severe social stigma and economic consequences from having conspicuous disabilities have been well-documented and articulated [Refs. 5, 9-13], highlighting the need for a low-cost prosthesis that enables able-bodied gait to mitigate discrimination and increases metabolic efficiency.

International patent publication WO 2016/179281, the entire contents of which are hereby incorporated by reference herein for all purposes, discloses a passive artificial knee that includes a locking hinge assembly. A ground reaction force applied to the artificial knee posterior to a locking axis of the locking hinge assembly causes an interfering relation by compression of the locking hinge assembly and a knee hinge assembly during heel strike at an early stance gait phase, thereby locking rotation of a post about a knee axis. However, reliance on friction to lock the artificial knee makes the disclosed device unsuitable.

SUMMARY OF EMBODIMENTS

An embodiment of the present invention provides a prosthetic knee for mechanically coupling an upper leg to a lower leg. In use, the upper leg, the lower leg and the prosthetic knee are subject to a ground reaction force that acts through a center of pressure on a foot attached to the lower leg. Orientation of the ground reaction force varies in space as a result of a gait. The prosthetic knee includes a prosthetic knee joint and a latch. The prosthetic knee joint is configured to couple to the upper leg. The prosthetic knee joint is also configured to pivot about a knee joint pivot axis. The latch is configured to couple to the lower leg. The latch is also configured to pivot about a virtual lock axis. The virtual lock axis is distinct from the knee joint pivot axis. The virtual lock axis is positioned such that the ground reaction force is posterior to the virtual lock axis in an early stance phase of the gait and the ground reaction force is anterior to the virtual lock axis in a late stance phase of the gait.

The latch includes a hook, and the latch defines a first notch. The first notch is engagable by the hook. When the first notch is engaged by the hook, the latch locks the prosthetic knee joint. The latch is also configured to automatically and purely mechanically disengage from the notch to unlock the prosthetic knee joint in response to the ground reaction force being anterior to the virtual lock axis, thereby permitting the prosthetic knee joint to pivot. The latch is also configured to automatically return to an engaging position in response to the pivot of the prosthetic knee joint.

Optionally, the prosthetic knee also includes an early stance flexion module. The early stance flexion module includes an early stance flexion joint. The early stance flexion joint is configured to pivot about an early stance flexion axis. The early stance flexion axis is distinct from the knee joint pivot axis, and the early stance flexion axis is distinct from the virtual lock axis. The early stance flexion axis pivotally couples the upper leg to the prosthetic knee joint about the early stance flexion axis. Position of the early stance flexion axis is adjustable, relative to position of the knee joint pivot axis. Torsional stiffness of the early stance flexion joint is adjustable.

Optionally, in any embodiment of the prosthetic knee, the early stance flexion module may be configured to apply an adjustable preload torque that must be overcome to pivot the early stance flexion joint about the early stance flexion axis.

Optionally, any embodiment of the prosthetic knee may also include a hydraulic damper coupled to dampen the pivot of the prosthetic knee joint about the knee joint pivot axis. The hydraulic damper may be configured to provide at least 1.1 times as much damping during flexion of the prosthetic knee joint as during extension of the prosthetic knee joint. Optionally, the hydraulic damper may be configured to provide at least 1.5, 2, 3 or 4 times as much damping during flexion of the prosthetic knee joint as during extension of the prosthetic knee joint.

Optionally, in any embodiment of the prosthetic knee, the hydraulic damper may include a linear hydraulic damper that includes a piston and at least one one-way valve.

Optionally, in any embodiment of the prosthetic knee, the hydraulic damper may include a first rotary hydraulic damper and a second rotary hydraulic damper. The first rotary hydraulic damper is mechanically coupled via a first one-way clutch to the prosthetic knee joint. The second rotary hydraulic damper is mechanically coupled to the prosthetic knee joint.

Optionally, the second rotary hydraulic damper may be mechanically coupled to the prosthetic knee joint via a second one-way clutch. The first and second one-way clutches are configured to rotate in opposite directions.

Optionally, each rotary hydraulic damper of the first and second rotary hydraulic dampers may include a cylinder that has an inner wall. The inner wall defines a volume. An axle may be longitudinally disposed within the cylinder for rotation therewithin, relative to the cylinder. A rotor may be mechanically coupled to the axle for rotation therewith. The rotor may have an outer surface spaced apart from the inner wall. A hydraulic fluid may be disposed within a volume defined between the inner wall and the outer surface.

Optionally, each rotary hydraulic damper of the first and second rotary hydraulic dampers may include a housing. An axle may be longitudinally disposed within the housing for rotation therewithin, relative to the housing. A plurality of longitudinally spaced apart first plates may be mechanically coupled to the axle for rotation therewith. A plurality of second plates may be rigidly coupled to the housing. The plurality of second plates may be interdigitated with the plurality of longitudinally spaced apart first plates so as to define respective volumes between adjacent pairs of first and second plates, and collectively define a total inter-plate volume. A hydraulic fluid may be disposed within the total inter-plate volume.

Optionally, the hydraulic damper includes a first rotary hydraulic damper and a second rotary hydraulic damper. At least one of the first and second rotary hydraulic dampers may include a directionally-dependent rotary hydraulic damper. The directionally-dependent rotary hydraulic damper may include a cylinder having an inner wall. The inner wall may define a volume. A hydraulic fluid may be disposed within the volume. An axle may be longitudinally disposed within the cylinder for rotation therewithin, relative to the cylinder. At least one fin may be spaced apart from the inner wall. The fin may be mechanically coupled to the axle by a spring for rotation with the axle. The fin and the spring may be configured to deflect the spring in response to a shear force of the hydraulic fluid, between the fin and the inner wall, as a result of rotation of the axle in a first direction, and thereby increase spacing between the fin and the inner wall. A stop may be configured to at least limit deflection of the spring when the axle rotates in a direction opposite the first direction.

Optionally, each fin of the at least one fin comprises a portion, less than all, of a cylinder and is disposed parallel to the inner wall.

Optionally, any embodiment of the prosthetic knee may include a four-bar linkage. The four-bar linkage may include a ground link, two grounded links, a floating link and four rotating joints. The ground link may be configured to mechanically couple to the lower leg. The floating link may be mechanically coupled to the prosthetic knee joint and the latch. The latch may pivots about the virtual lock axis as a result of pivoting of the two grounded links about two respective rotating joints of the four rotating joints.

Optionally, positions of at least two rotating joints of the four rotating joints may be adjustable to alter position of the virtual lock axis.

Optionally, any embodiment of the prosthetic knee may include a swing extension energy storage module. The swing extension energy storage module may include a third spring. The third spring may be configured to deflect in response to pivoting of the prosthetic knee joint. The third spring may be deflected when the first notch is engaged by the hook. When deflected, the third spring may urge the prosthetic knee joint to pivot about the knee joint pivot axis so as to increase knee flexion angle of the prosthetic knee joint.

Optionally, in any embodiment of the prosthetic knee, the latch may be configured to automatically engage when the prosthetic knee joint returns to an angle of between about 0° and about 10 of knee flexion.

Optionally, in any embodiment of the prosthetic knee, the latch may be configured to automatically engage at at least two distinct points (a double latch). When the latch is engaged at a second of the at least two distinct points, the prosthetic knee joint is bent at an angle of between about 1° and about 15° of knee flexion. When the latch is engaged at a first of the at least two distinct points, the prosthetic knee joint is bent at an angle of between about 0° and about 1° of knee flexion.

Optionally, the latch defines a second notch that is engagable by the hook. When the hook is engaged in the first notch, the latch is engaged at the first of the at least two distinct points. When the hook is engaged in the second notch, the latch is engaged at the second of the at least two distinct points.

Optionally, in any embodiment of the prosthetic knee, the virtual lock axis may be disposed along an imaginary line extending through the knee joint pivot axis and a ground reaction force transition point. The ground reaction force transition point may correspond to a location of the center of pressure when the prosthetic knee initiates late stance flexion.

The foot has a length. Optionally, the ground reaction force transition point may be located between: (a) about 5% of the length of the foot from a toe of the foot and (b) about 5% of the length of the foot from a heel of the foot.

Optionally, the virtual lock axis may be disposed a distance about $r=\theta/s$ from the knee joint pivot axis along the imaginary line, where s equals a distance the latch moves to disengage and $\theta$ is less than about 1°.

Another embodiment of the present invention provides a directionally-dependent rotary hydraulic damper. The directionally-dependent rotary hydraulic damper includes a cylinder. The cylinder has an inner wall. The inner wall defines a volume. A hydraulic fluid is disposed within the volume. An axle is longitudinally disposed within the cylinder for rotation therewithin, relative to the cylinder. At least one fin is spaced apart from the inner wall. The fin is mechanically coupled to the axle by a spring for rotation with the axle. The fin and the spring are configured to deflect the spring in response to a shear force of the hydraulic fluid, between the fin and the inner wall, as a result of rotation of the axle in a first direction, and thereby increase spacing between the fin and the inner wall. A stop is configured to at least limit deflection of the spring when the axle rotates in a direction opposite the first direction.

Yet another embodiment of the present invention provides an early stance flexion module for a prosthetic knee that mechanically couples an upper leg to a lower leg. The prosthetic knee has a lock axis and a prosthetic knee joint. The prosthetic knee joint pivots about a knee joint pivot axis. The early stance flexion module includes an early stance flexion joint. The early stance flexion joint is configured to pivot about an early stance flexion axis. The early stance flexion axis is distinct from the lock axis. The early stance flexion axis is also distinct from the knee joint pivot axis. The early stance flexion joint pivotally couples the upper leg to the prosthetic knee joint about the early stance flexion axis. Position of the early stance flexion axis is adjustable, relative to position of the knee joint pivot axis. Torsional stiffness of the early stance flexion joint is adjustable.

An embodiment of the present invention provides a pivot for a knee joint latch in a prosthetic knee. The prosthetic knee mechanically couples an upper leg to a lower leg via a prosthetic knee joint. The knee joint latch automatically locks and unlocks the prosthetic knee joint during a user's gait. The pivot includes a four-bar linkage. The four-bar linkage includes a ground link, two grounded links, a floating link and four rotating joints. The ground link is configured to mechanically couple to the lower leg. The floating link is mechanically coupled to the prosthetic knee joint and the knee joint latch. The knee joint latch pivots about a virtual lock axis as a result of pivoting of the two grounded links about two respective rotating joints of the four rotating joints.

Another embodiment of the present invention provides a swing extension energy storage module for a prosthetic knee. The prosthetic knee includes a prosthetic knee joint that pivots about a knee joint pivot axis. A knee joint latch automatically locks and unlocks the prosthetic knee joint during a user's gait. The swing extension energy storage module includes a spring. The spring is configured to deflect in response to pivoting of the prosthetic knee joint. The spring is deflected when the knee joint latch locks. When deflected, the spring urges the prosthetic knee joint to pivot about the knee joint pivot axis so as to increase knee flexion angle of the prosthetic knee joint.

Other embodiments of the present invention include any combination of: a prosthetic knee; an early stance flexion module; a hydraulic damper, such as a linear hydraulic damper or a rotary hydraulic damper, such as a directionally-dependent rotary hydraulic damper; a swing extension energy storage module; a double latch; and/or a pivot for a knee joint latch that pivots about a virtual lock axis, such as a pivot for a knee joint latch implemented with a four-bar linkage.

BRIEF DESCRIPTION OF THE DRAWINGS

The invention will be more fully understood by referring to the following Detailed Description of Specific Embodiments in conjunction with the Drawings, of which:

FIG. 4 shows the stance stability module in a locked configuration, in which the prosthetic knee is locked and cannot, therefore, pivot, according to an embodiment of the present invention.

FIG. 5 shows the stance stability module unlocking, according to an embodiment of the present invention.

FIG. 6 shows the stance stability module 300 repositioning, in preparation for relocking, according to an embodiment of the present invention.

FIG. 7 shows the stance stability module 300 relocking, according to an embodiment of the present invention.

DETAILED DESCRIPTION OF SPECIFIC EMBODIMENTS

Embodiments of the present invention provide a passive prosthetic knee that enables a leg amputee to have an able-bodied gait, thereby reducing metabolic cost and mitigating socio-economic discrimination. The prosthetic knee includes one or more of several modules, each module providing a different mechanical feature that improves the user's gait.

Gait Biomechanics Vocabulary

The terms force, vector, moment and torque have their respective common meanings from physics. A force, such as a ground reaction force, has a magnitude and a direction. Thus, a force can be represented by a vector. A moment is an expression involving a product of a distance and a physical quantity, and in this way a moment accounts for how the physical quantity is located or arranged. For example, a moment of force acting on an object, often called torque, is the product of the force and the distance from a reference point.

A spring is an elastic object that stores mechanical energy. Examples of springs include compression springs, extension springs and torsion springs. Resilient materials, such as resilient foam, can be used as springs, thus the term "spring," as used herein, includes such materials.

A flexure is a flexible element, or combination of elements, engineered to be compliant in one or more specific degrees of freedom.

As used herein, "active" means externally powered, such as by a battery, as opposed to "passive," which means unpowered, except possibly by a spring that stores or accumulates energy from mechanical operation of a prosthesis driven by its human user during a portion of a gait cycle and that releases some of the stored energy during another portion of the gait cycle.

As used herein, "posterior" means behind, relative to the normal direction of forward walking of a human being, and "anterior" means in front of, relative to the normal direction of forward walking of a human being.

Figure 1:
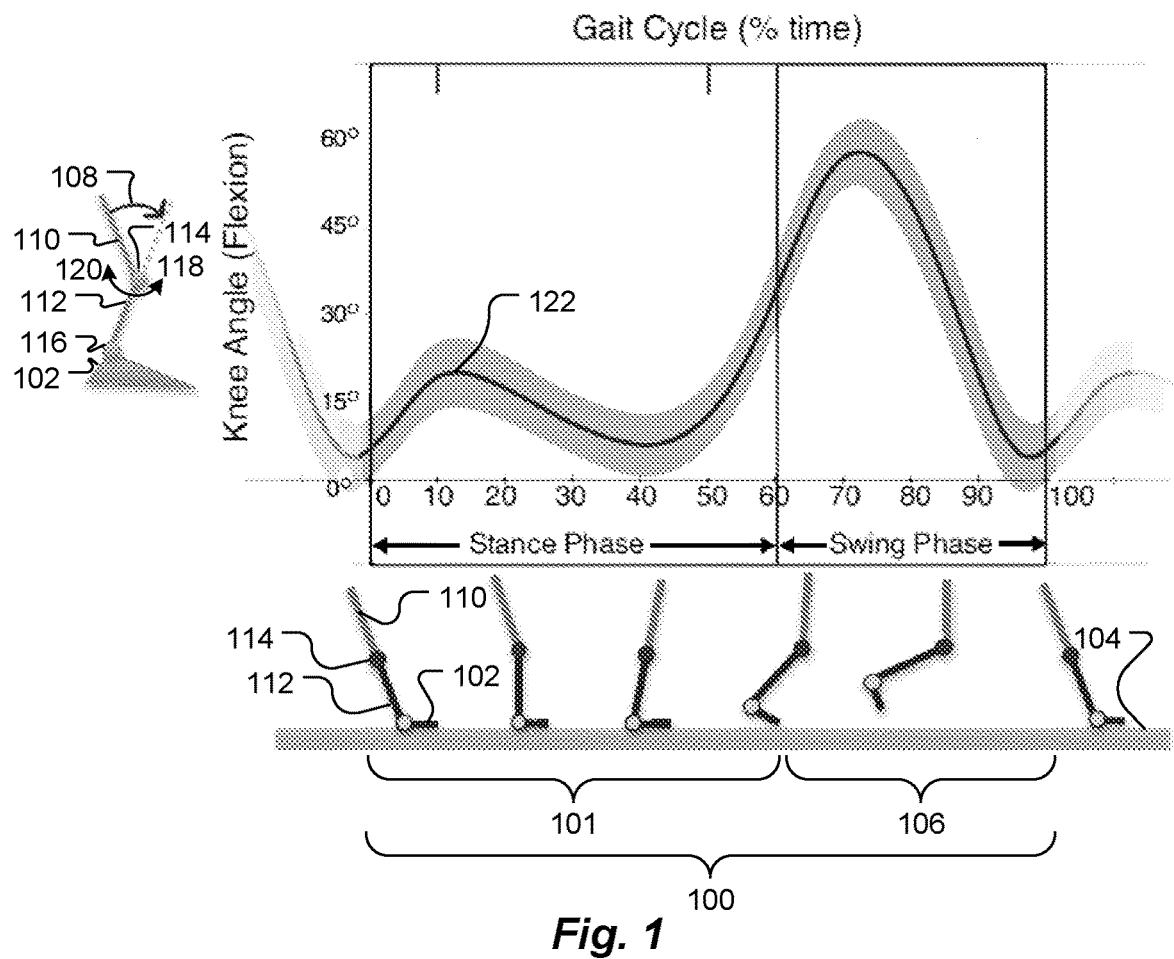
FIG. 1 is a schematic diagram illustrating a human gait, including a stance phase and a swing phase, as well as a graph of a knee flexion angle at selected points along the gait, as known from the prior art, and a point to which early stance flexion should be accommodated, according to an embodiment of the present invention.
Figure 2:
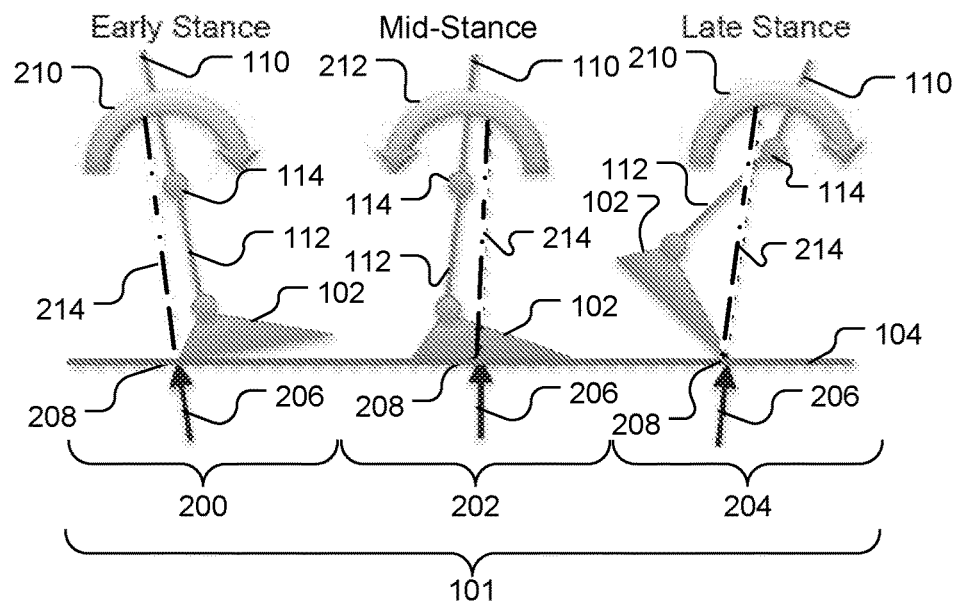
FIG. 2 is a schematic diagram illustrating three portions of the stance phase of FIG. 1, specifically an early stance portion, a mid-stance portion and a late stance portion, as known from the prior art.

A brief summary of terms related to human gait biomechanics used herein are described briefly, with reference to FIGS. 1 and 2. As schematically illustrated in the bottom of FIG. 1, a human gait cycle 100 of each leg is divided into a stance phase 101, during which a foot 102 is in contact with the ground 104, followed by a swing phase 106, during which the foot 102 leaves contact with the ground 104 for clearance. A knee flexion angle 108 (shown to the left of the graph in FIG. 1) is defined as a relative angle between an upper leg 110 and a lower leg 112. A knee joint 114 and an ankle joint 116 are also shown. An extension direction 118 at the knee joint 114 is defined as a direction of rotation of the knee joint 114 so as to straighten the leg, and to be opposite a flexion direction 120.

FIG. 2 schematically illustrates the stance phase 101, including an early stance portion 200, a mid-stance portion 202 and a late stance portion 204. A ground reaction force (GRF) 206, acting through a center of pressure (COP) 208, results in a flexion moment 210 or an extension moment 212 about the knee joint 114 through the stance phase 101. To assist in understanding the force causing the flexion moment 210 and the extension moment 212, the ground reaction force 206 vector is extended by a dashed line 214.

The graph in FIG. 1 plots normative knee angle 108 kinematics through the gait cycle 100, along with a standard deviation therefrom shown in a grey band [Ref. 14]. The schematic illustration below the horizontal axis of the graph shows corresponding upper leg 110 and lower leg 112 trajectories through the gait cycle 100.

Described herein are design, analysis and bench-level testing of several major functional modules of a new prosthetic knee architecture, including: (1) a four-bar latch mechanism for achieving stability during the stance phase 101 of walking, (2) an early stance 200 flexion module designed by implementing a fully adjustable mechanism, (3) a hydraulic damping system for achieving smooth and reliable swing phase 106 control and (4) a swing extension energy storage module. Embodiments of the present invention include one or more of these modules to provide a fully passive prosthetic knee that enables transfemoral amputees to have an able-bodied gait 100. Such embodiments may be of particular interest in developing countries. Basic operation and architecture of prosthetic knees are described by Narang, Arelekatti and Winter [Refs. 1-5].

Prior Art and its Limitations

A significant cost-performance gap exists in the realm of current knee prostheses. Advanced, high-performance prosthetic devices used in the developed world are typically active in order to achieve optimal performance, making them inappropriate for the developing world in terms of cost, as well as sub-optimal for large-scale, resource-constrained application [Refs. 5, 15, 16]. Typical developing world prostheses are passive and low-cost, but primitive in functionality, inhibiting able-bodied gait 100 and garnering poor user satisfaction [Refs. 12, 15]. Manually locked knees are currently the most widely distributed prosthetic knees in developing countries.

A four-bar polycentric knee is currently being adopted in India and other countries, and shows better performance than previous single-axis joints [Ref. 12]. While similar knees have shown better performance than locked or single-axis devices, they notably fail to address early stance 200 flexion or proper timing in later stance 204 flexion [Ref. 5]. The LCKnee prosthetic knee joint designed by Andrysek et al. [Refs. 17, 18], with a reliable single-axis mechanical latch, addresses complaints of falling due to buckling in other devices. However, early stance 200 flexion and swing phase 106 damping required for able-bodied kinematics [Ref. 5] have not been satisfactorily addressed.

Recent work by Arelekatti and Winter [Refs. 3, 5] moved towards development of a low-cost passive prosthetic knee, addressing these outstanding needs and allowing for an efficient walking gait 100. By modeling knee angle 108, moment and power over the course of a gait cycle 100, it was determined that a close approximation of healthy knee function could be achieved passively using a spring activated at early stance 200 and two dampers activated over the course of the late stance 204 and swing 106 phases [Refs. 1, 2]. This analysis was used to develop low-cost, passive prostheses [Refs. 3-5] with automatic stance phase locks for stability. The prostheses were tested on four above-knee amputees.

However, desired early stance 200 flexion was not observed in amputee gaits, despite incorporating a necessary elastic module. Additionally, these prostheses relied on zero-order dampers (using friction brakes) and a friction-based automatic latch for stability during early stance 200. This reliance on friction made the prostheses unsuitable for long term use [Ref. 5].

Main Modules

Embodiments of the present invention include improvements that address the main deficits identified in the earlier prostheses. One goal in developing these embodiments was to deterministically enable desired gait kinematics, working specifically on three aspects identified to be problematic in the previous prostheses: stance 101 stability, early stance 200 flexion and swing phase 106 control. Some embodiments of the present invention include one or more of four modules (a stance stability module, an early stance flexion module, a swing phase control module and a swing extension energy storage module), each of which is described herein. Results of testing embodiments are discussed together for the first two modules and separately for the third module.

Stance Stability Module

Stance stability is a critical function of a prosthetic knee, as it is directly related to user safety. The main design requirements for the stance stability module are: an ability to withstand a flexion moment of at least about 40 Nm (caused by the ground reaction force 206) without buckling; allowing quick transition into the swing phase 106; ensuring the mechanism is latched before heel strike; and controlling backlash in the mechanism to prevent hyperextension (to within about 1°) [Ref. 7]. Hyperextension is knee extension backwards from a neutral standing position. Various locking and braking mechanisms for single and multiple axis knees were considered before it was decided to focus on implementing a single-axis, automatically locking mechanism [Ref. 17]. This strategy was chosen for its stability, simplicity and durability.

Figure 3:
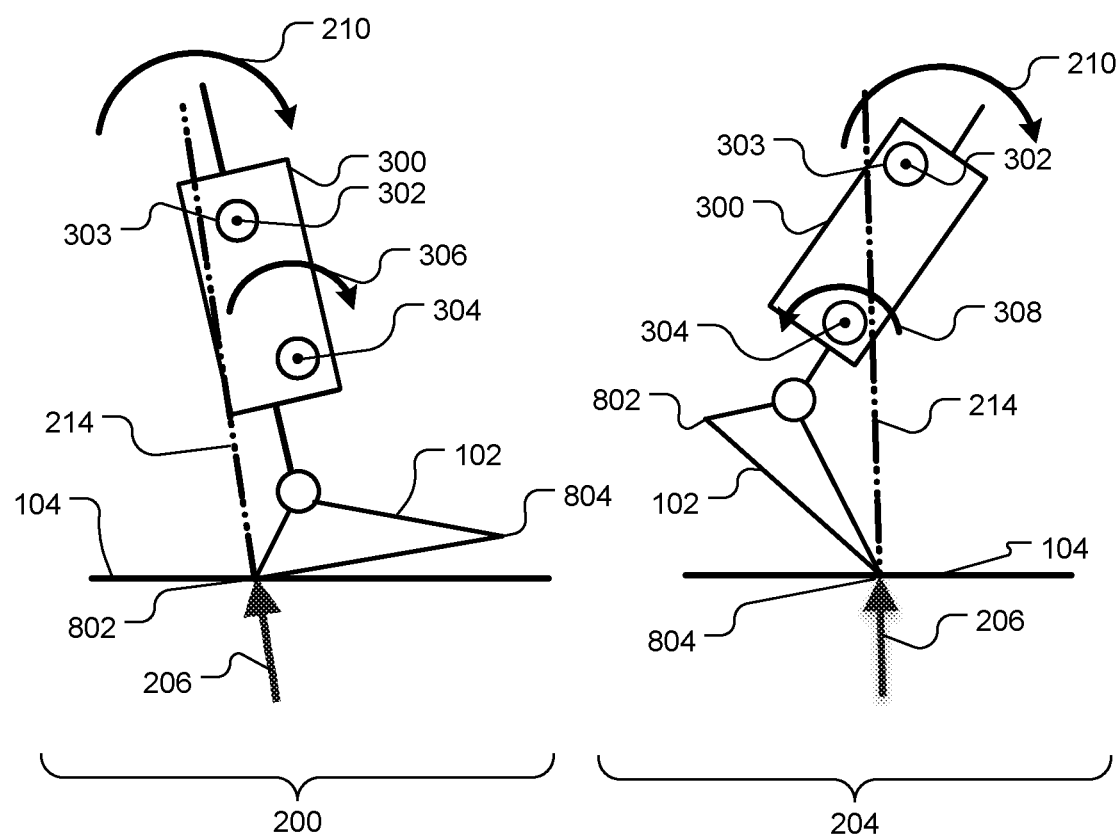
FIG. 3 schematically illustrates aspects of a stance stability module during early stance and late stance phases of the human gait, including a ground reaction force causing flexion moments about both a prosthetic knee joint axis (knee joint pivot axis) and a virtual lock axis in the early stance phase, and the ground reaction force causing a flexion moment about the knee joint pivot axis but an extension moment about the lock axis in the late stance phase, according to an embodiment of the present invention.

FIG. 3 schematically illustrates aspects of the stance stability module 300 during early stance 200 and late stance 204. The prosthetic knee pivots about a knee joint pivot axis 302. In an able-bodied gait cycle 100 (FIG. 1), the knee 114 (FIG. 1) experiences a flexion moment 210 (FIG. 3) during both the early stance 200 and the late stance 204 phases. In the early stance 200, a prosthetic knee joint 303 (FIG. 3) must stay locked to prevent buckling, while in the late stance 204 the prosthetic knee joint 303 should be unlocked to initiate swing.

An innovative solution uses a knee joint locking latch mounted to pivot on a lock axis 304, distinct from the knee joint pivot axis 302 [Ref. 15]. Location of the lock axis 304 is selected, relative to the ground reaction force 206 and the knee joint pivot axis 302, such that the ground reaction force 206 is posterior to the lock axis 304 in the early stance 200, and anterior to the lock axis 304 in the late stance 204.

The different positions of the ground reaction force 206 can be used to automatically engage and disengage the latch. Similar to a latch design by Andrysek [Ref. 17], this strategy was implemented in Arelekatti and Winter's previous design [Refs. 3-5] with some success. However, we realized the previous design could be significantly improved by switching from using a physical lock axis to a virtual lock axis. A four-bar implementation of this virtual lock axis is discussed in more detail herein.

Mechanical Design

Figure 4:
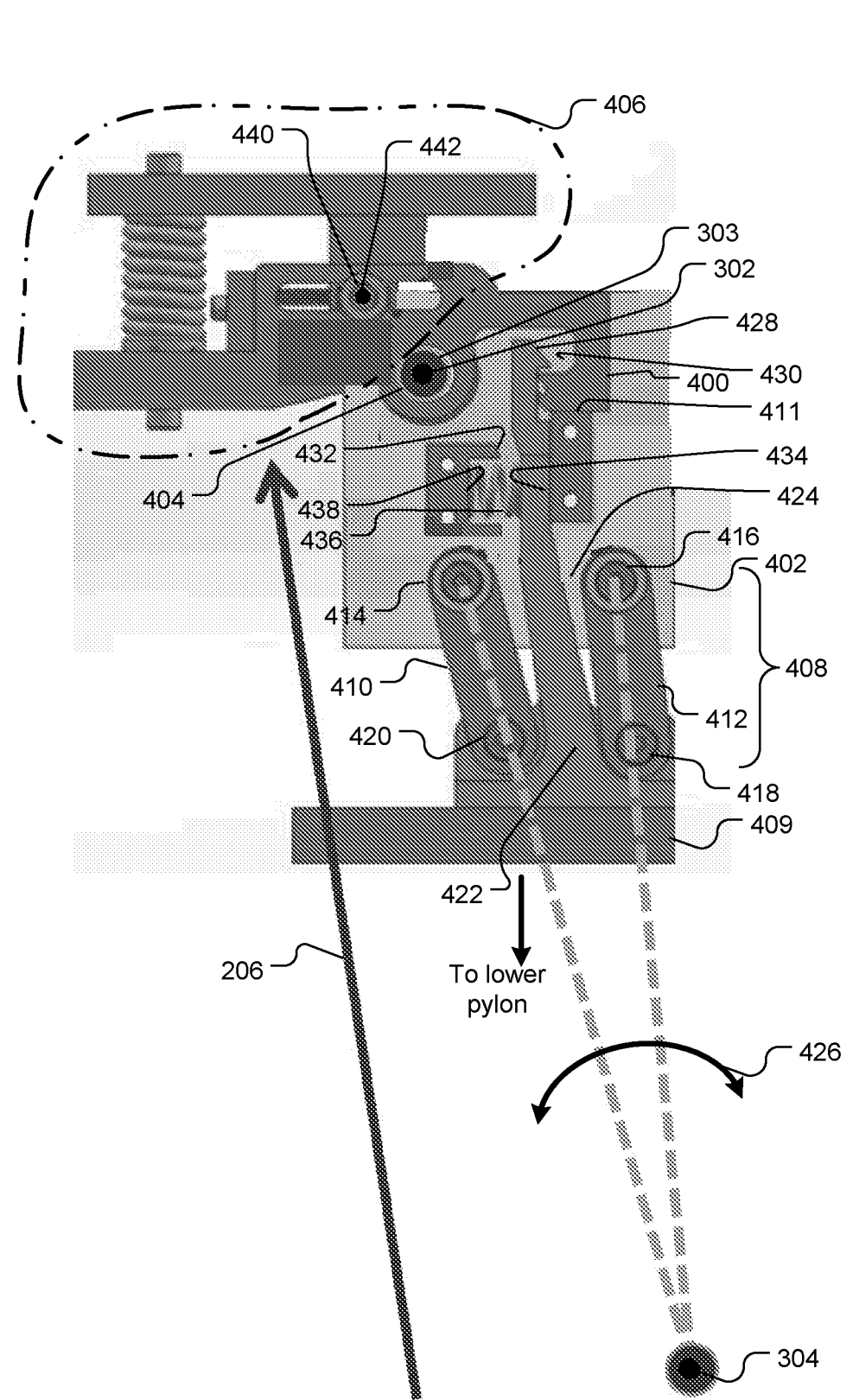
FIGS. 4-7 illustrate the stance stability module of FIG. 3 and an early stance flexion module at respective key points during the gait cycle of FIG. 1, according to an embodiment of the present invention.
Figure 5:
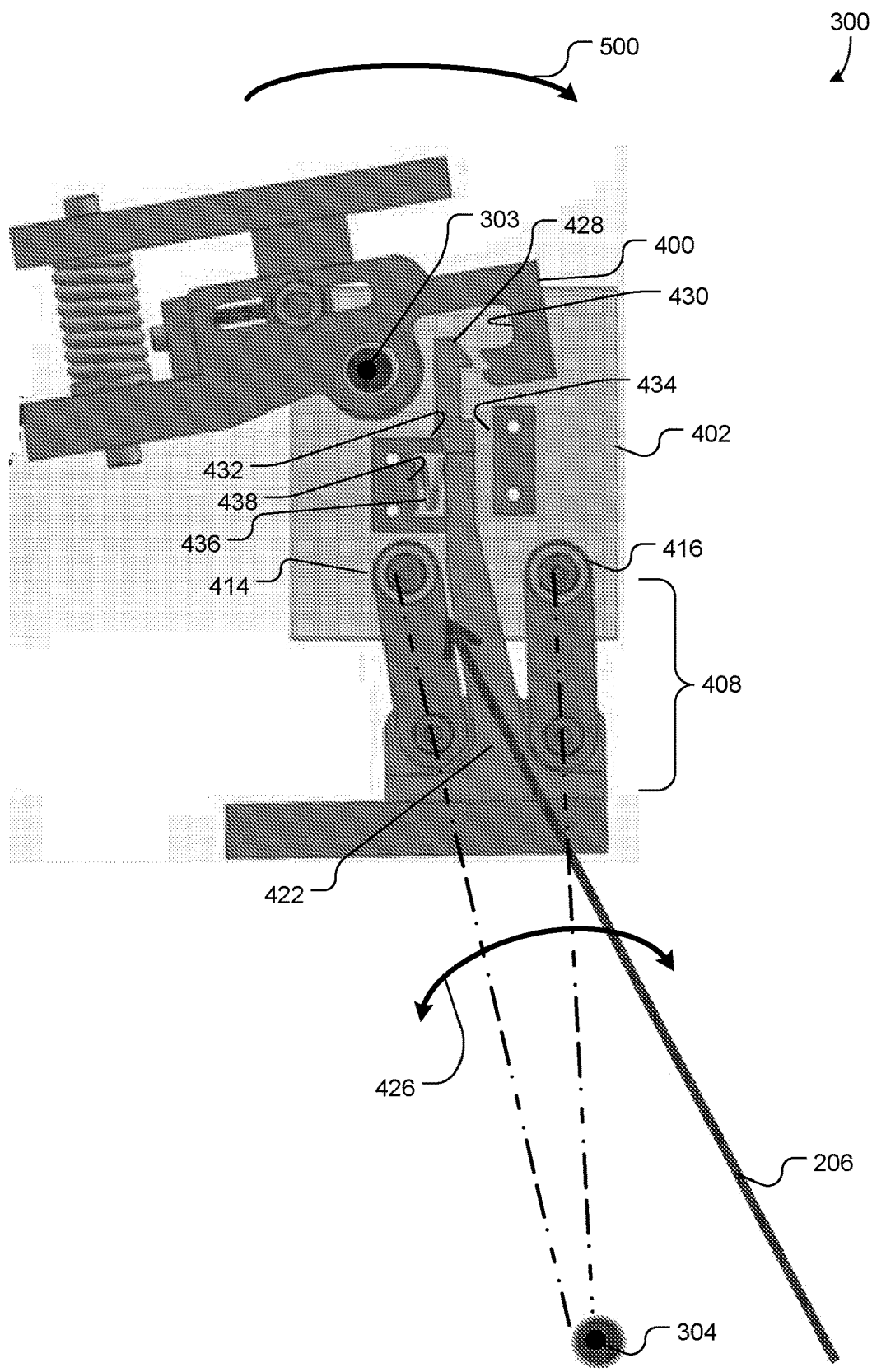
Figure 6:
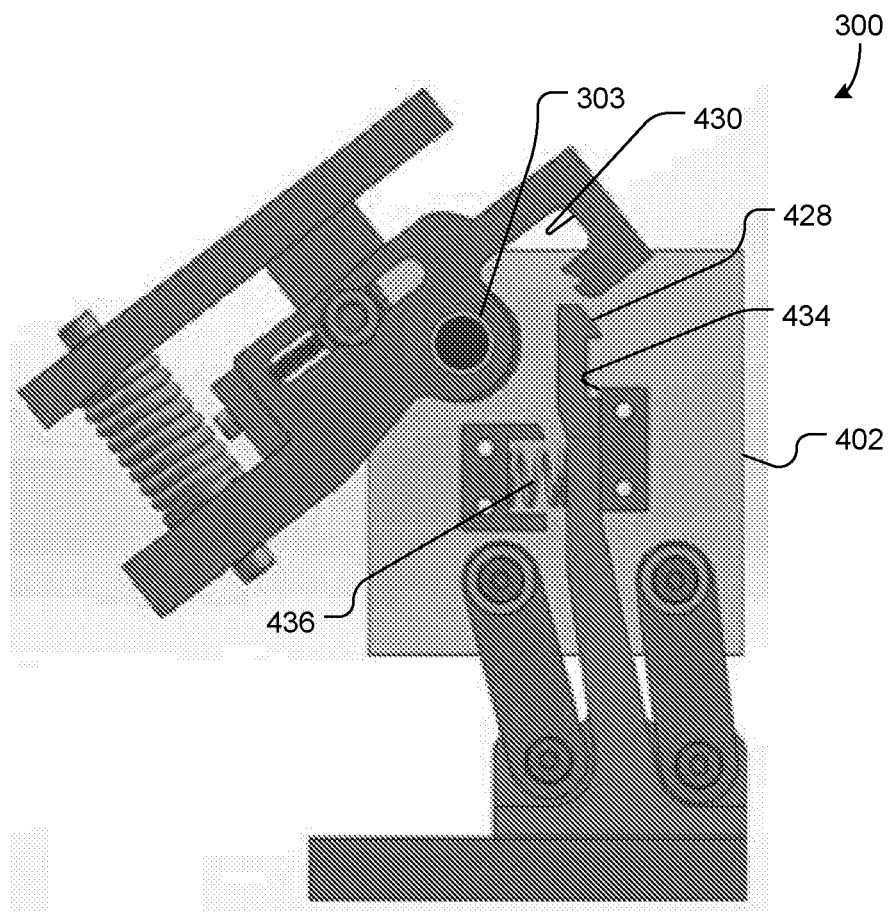
Figure 7:
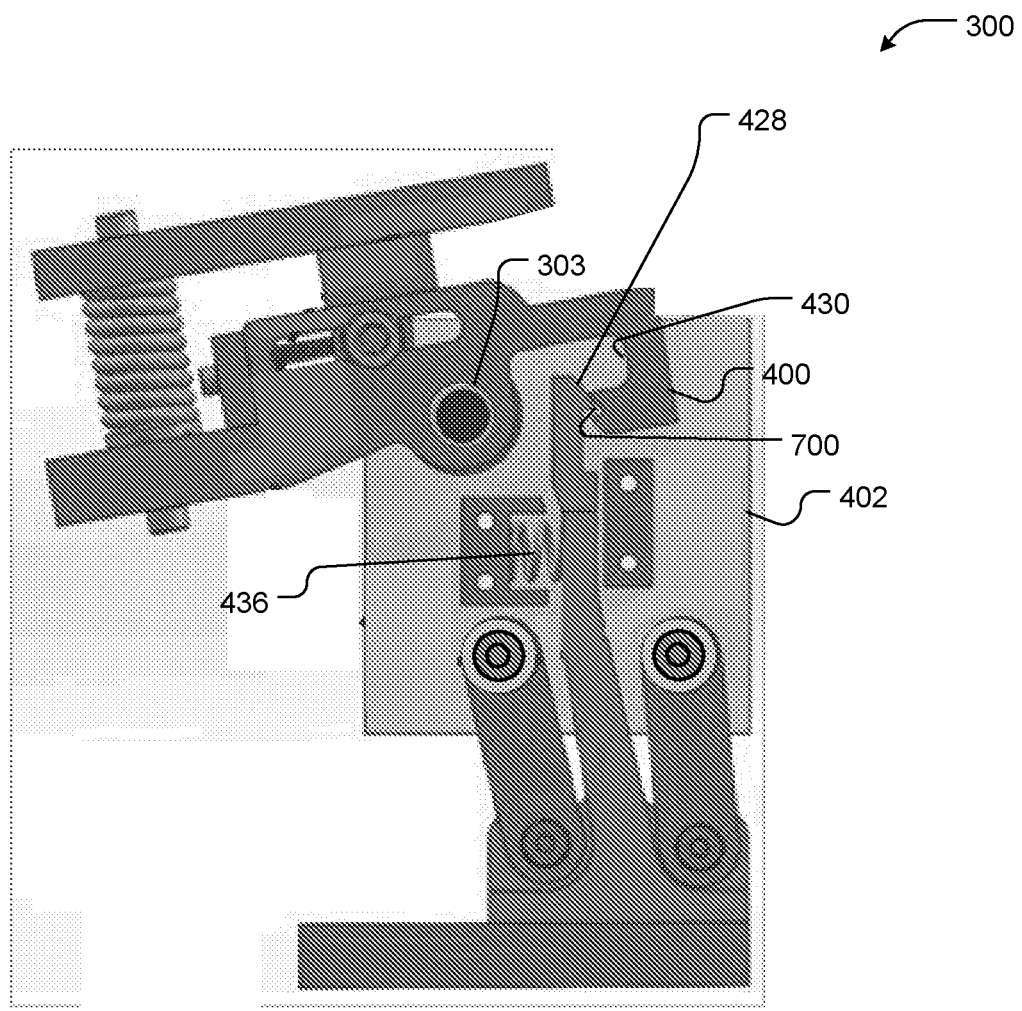

Sectional views of the stance stability module 300 are shown in FIGS. 4-7 at respective key points during the gait cycle 100 (FIG. 1). FIG. 4 shows the stance stability module 300 in a locked mode, in which the prosthetic knee is locked and cannot, therefore, pivot. FIG. 5 shows the stance stability module 300 in an unlocking mode. FIG. 6 shows the stance stability module 300 in a repositioning mode, in preparation for relocking. FIG. 7 shows the stance stability module 300 in a relocking mode.

Returning to FIG. 4, a knee piece 400 is pivotally coupled to the latch 402 via a pin 404, which acts as a prosthetic knee joint 303 (see also FIG. 3). The knee piece 400 is mechanically coupled to the early stance flexion module 406, which is mechanically coupled to a socket (not shown) for receiving an upper leg stump. The latch 402 is mechanically coupled via a four-bar linkage 408 to a lower member 409, which is mechanically coupled to a lower pylon (not shown) and, via the lower pylon, to a prosthetic foot.

The pin 404 may be made of steel or another suitable material. Thus, the knee piece 400 can pivot, relative to the latch 402, about the pin 404 (prosthetic knee joint 303). The knee joint pivot axis is shown at 302. A first hard stop 411 limits clockwise (as viewed in FIGS. 4-7) rotation of the prosthetic knee joint 303. As used herein, "pivotally coupled" means mechanically coupled so as to provide rotational or approximately rotational motion in at least one dimension. The motion need not be purely rotational. The motion may, for example, include some parasitic motion, such as translation. Thus, in some embodiments, the prosthetic knee joint 303 may be implemented with a living hinge, cross-flexure joint or other flexure bearing. In some embodiments, the prosthetic knee joint 303 may be implemented with a ball and socket or any other suitable compliant joint that provides a pivotal coupling.

The four-bar linkage 408 includes two grounded links 410 and 412 and four rotating joints 414, 416, 418 and 420. A portion of the lower member 409 between two of the rotating joints 418 and 420 forms a ground link 422 of the four-bar linkage 408, and a portion of the latch 402 between the other two rotating joints 414 and 416 forms a floating link 424 of the four-bar linkage 408. Thus, the latch 402 pivots about the virtual lock axis 304, as indicated by double-headed arrow 426. Optionally, the position of the virtual lock axis 304 may be made discretely or infinitely adjustable, as described herein.

The latch 402 includes a hook 428, and the latch 402 defines a first notch 430 that may be engaged by the hook 428. The first notch 430 is defined by the knee piece 400, which pivots about the prosthetic knee joint 303. The hook 428 is rigidly attached to the ground link 422 of the four-bar linkage 408. Thus, as the latch 402 pivots 426 about the virtual lock axis 304, the hook 428 can be seen as pivoting, relative to the latch 402, between a second hard stop 432 and a third hard stop 434. The two hard stops 432 and 434 are fixed, relative to the latch 402. A first spring 436 is bounded on one side by a spring stop 438 that is also fixed relative to the latch 402. The first spring 436 urges the hook 428, and therefore the ground link 422 and thus the lower pylon, toward the right, as seen in FIG. 4.

When the hook 428 is positioned against the third hard stop 434 and engaged with the first notch 430, as shown in FIG. 4, the hook 428, and therefore the latch 402, prevents the knee piece 400 pivoting, thereby locking the prosthetic knee joint 303. The hook 428 does not rely on friction to capture the first notch 430. Thus, the latch 402 locks the prosthetic knee joint 303 without relying on friction, as in the artificial knee disclosed in WO 2016/179281. However, as shown in FIG. 5, when the hook 428 is positioned against the second hard stop 432, the hook 428 is not engaged with the first notch 430, and the prosthetic knee joint 303 is able to pivot.

Operation of the latch 402 involves four major steps shown in FIGS. 4-7, respectively. The first two steps (FIGS. 4 and 5) occur the during stance phase 101 (FIG. 1), and the latter two steps (FIGS. 6 and 7) occur during the swing phase 106 (FIG. 1). In the locked mode (FIG. 4), when a user's heel first strikes the ground 104 (FIG. 2), the prosthetic knee joint 303 (FIGS. 3 and 4) experiences a flexion moment 210, but the latch 402 (FIG. 4) is locked. Thus, flexion pivoting of the prosthetic knee joint 303 is prevented by mechanical engagement of the hook 428 and the first notch 430.

Figure 8:
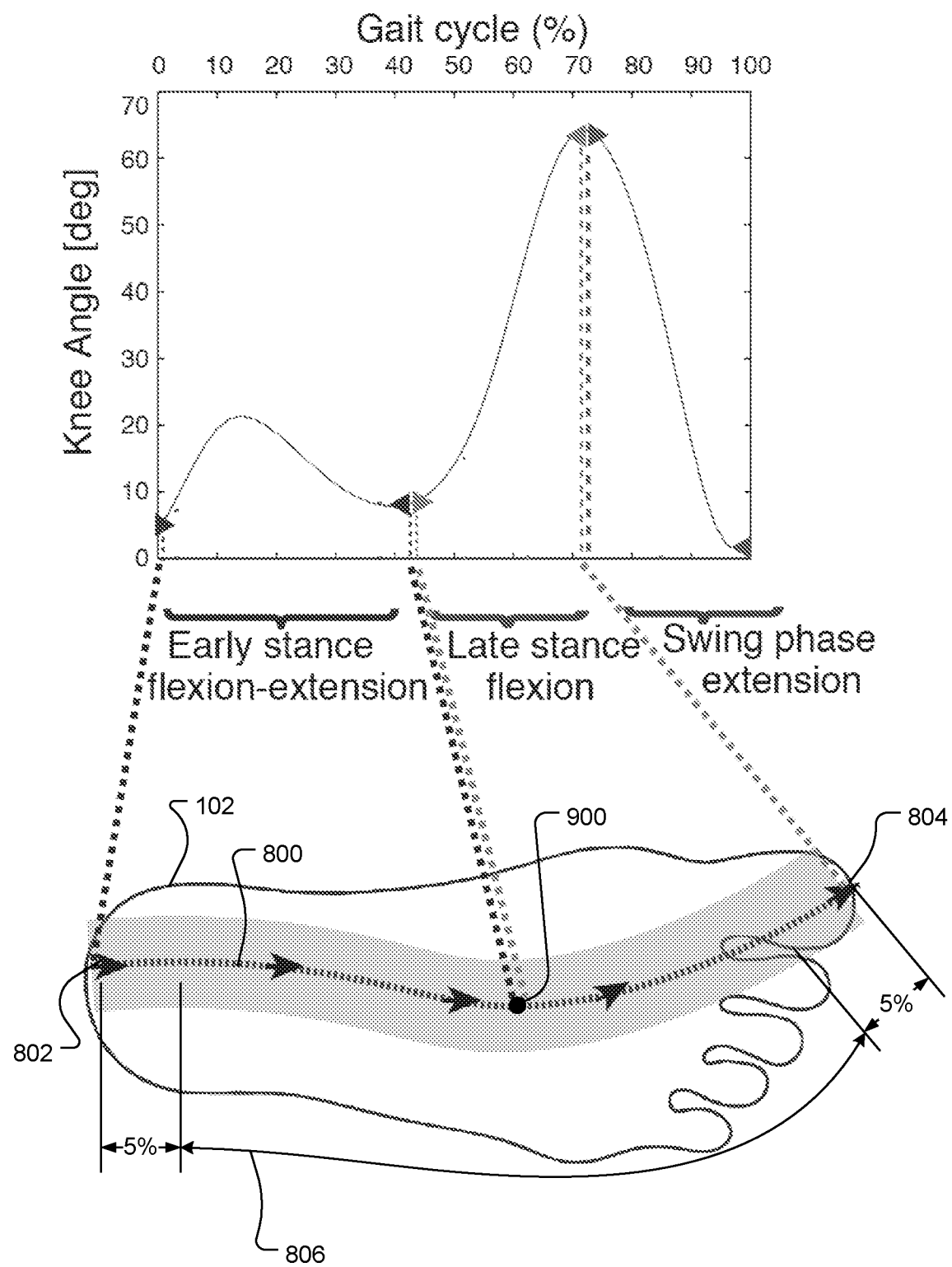
FIG. 8 schematically illustrates movement of a center of pressure on a foot during the gait, as well as a graph plotting corresponding changes in the knee flexion angle, as known from the prior art, and placement of a ground reaction force transition point near the beginning of late stance flexion of the knee, according an embodiment of the present invention.

During the stance phase 101 (FIG. 2), the user's foot 102 rolls over the ground 104, from heel to toe. As shown in the bottom of FIG. 8, the center of pressure 208 follows a path 800 from the heel 802 to the toes or big toe 804. The ground reaction force 206 (FIG. 3) moves towards the toes 804, and the direction of the ground reaction force 206 vector varies. As evident in FIG. 4, at the beginning of the early stance 200 (FIG. 2), the ground reaction force 206 is posterior to the virtual lock axis 304. The ground reaction force 206 presses the knee piece 400 against the first hard stop 411, thereby relieving any pressure a side of the first notch 430 may have exerted on the hook 428, allowing the hook 428 to subsequently move away from the first notch 430, free of sliding friction against the side of the first notch 430.

As can be seen in FIG. 5, when the ground reaction force 206 passes anterior to (i.e., to the right of, as viewed in FIG. 5) the virtual lock axis 304, the latch 402 pivots 500 about the virtual lock axis 304 toward the right (as viewed in FIG. 5), relative to the ground link 422 of the four-bar linkage 408, taking with it two of the rotating joints 414 and 416, the knee piece 400, the notch 430, the two hard stops 432 and 434 and the spring stop 438. Since the hook 428 is rigidly attached to the ground link 422, the notch 430 disengages, toward the right, from the hook 428. However, within a reference frame of the latch 402, the hook 428 can be seen to disengage, toward the left, from the notch 430. Movement of the hook 428, relative to the spring stop 438, compresses the first spring 436.

With the latch 402 now in the unlocked position, the prosthetic knee joint 303 is allowed to rotate under a flexion moment 210 (FIG. 2) as the ground reaction force 206 passes back posterior to the knee joint pivot axis 302, but remains anterior to the virtual lock axis 304, during the late stance 204 (FIG. 3). Thus, the latch 402 is configured to automatically and purely mechanically, i.e., passively, disengage to unlock the prosthetic knee joint 303 in response to a moment caused by the ground reaction force 206 being anterior to the virtual lock axis 304, thereby permitting the prosthetic knee joint 303 to pivot.

As shown in FIG. 6, once the prosthetic knee joint 303 has flexed and swing is initiated, the first spring 436 forces the latch 428 back against the third stop 434, i.e., back to an engaging position, ready to catch and lock the notch 430 again. Thus, the latch 402 is configured to automatically return to an engaging position in response to the pivot of the prosthetic knee joint 303.

As the lower leg 112 (FIG. 1) and foot 102 swing forward to extend at the end of the gait cycle 100, the knee piece 400 comes down on the beveled end of the hook 428, as shown in FIG. 7, pushing back the hook 428 against the first spring 436 until the prosthetic knee joint 303 has pivoted far enough to allow the first spring 436 to press the hook 428 back into the notch 430, thereby relocking the prosthetic knee joint 303. In our prototype, the first spring 426 may have a stiffness of about 2-15 N/mm. However, in other embodiments, an appropriate spring stiffness may be calculated or determined empirically.

Optionally, the knee piece 400 defines a second notch 700. The second notch 700 allows the knee piece 400 to relock at two different points. We refer to such a latch 402 as a "double latch." The double latch allows the knee to lock at an intermediate point before reaching full extension, such as when the prosthetic knee joint 303 is bent at an angle of about 10° of knee flexion 108 (FIG. 1). The ability to lock at the intermediate point is important for user safety, because the knee locks even if the user does not fully extend the knee before heel strike, as may happen when walking up an incline.

Thus, the latch 402 is configured to automatically engage at at least two distinct points, such that when the latch 402 is engaged at a second of the at least two distinct points (the second notch 700), the prosthetic knee joint 303 is bent at an angle of between about 1° and about 15° of knee flexion 108, and when the latch 402 is engaged at a first of the at least two distinct points (the first notch 430), the prosthetic knee joint 303 is bent at an angle of between about 0° and about 1° of knee flexion 108. Thus, the latch 402 defines the second notch 700, which is engagable by the hook 428. When the hook 428 is engaged in the first notch 430, the latch 402 is engaged at the first of the at least two distinct points, and when the hook 428 is engaged in the second notch 700, the latch 402 is engaged at the second of the at least two distinct points.

Lock Axis Placement

In a normal gait 100, the center of pressure 208 of the ground reaction force moves from the heel 802 to the toe 804 [Ref. 14], as discussed with reference to FIG. 8. In embodiments of the present invention, the ground reaction force's orientation in space is deterministically used to unlock the latch 402 at a predetermined phase angle of the gait 100, also referred to herein as a "transition point." The transition point may encompass a single phase angle or a range of phase angles. As the ground reaction force 206 passes through the predetermined phase angle or range, the latch 402 switches from being engaged to being disengaged, allowing the prosthetic knee joint 303 to pivot and the lower leg 112 to swing.

Figure 9:
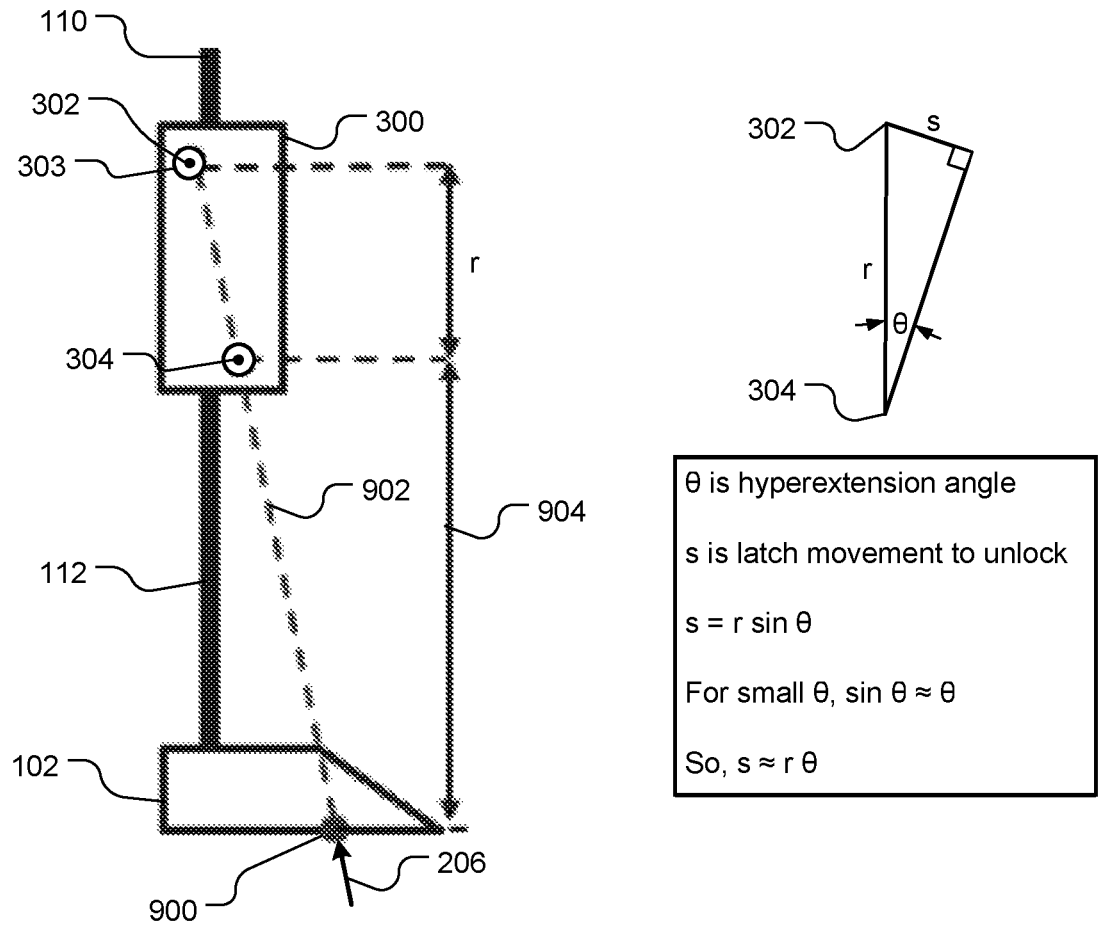
FIG. 9 is a schematic diagram illustrating placement of the virtual lock axis, relative to a knee joint pivot axis and the ground reaction force transition point, according to an embodiment of the present invention.

As shown schematically in FIG. 9, this ground reaction force transition point 900 may be determined by projecting an imaginary line 902 through the knee joint pivot axis 302 and the virtual lock axis 304, down to the foot 102. Thus, by determining a desired ground reaction force transition point 900, the placement of the virtual lock axis 304 may be limited to the line 902 connecting the ground reaction force transition point 900 and the knee joint pivot axis 302.

In order to imitate an able-bodied gait cycle 100, we determined that the ground reaction force transition point 900 should be placed at the center of pressure when the knee 114 initiates late stance flexion 204, as shown in FIG. 8. From Winter's gait data [Ref. 14], we decided the ground reaction force transition point 900 should be in a range 806 that extends between: (a) about 5% of the length of the foot 102 from the heel 802 and (b) about 5% of the length of the foot 102 from the toe 804. This range 806 allows for the great range of body dimensions of potential users. For some users, we found that the ground reaction force transition point 900 should be located about 17-19 cm from the heel 802 [Ref. 14].

Returning to FIG. 9, after deciding upon the ground reaction force transition point 900 and the line 902 through the virtual lock axis 304, the height 904 of the virtual lock axis 304 may be determined to reduce hyperextension, while maintaining stance stability. Hyperextension results in a small wobble the user feels as the latch 402 unlocks during mid-stance extension 202. The relationship between the hyperextension angle and latch unlocking movement can be modeled by a simple angle-arc length relationship:

$$s = r\theta \quad (1)$$

where s is the latch movement distance when the knee unlocks, r is the vertical distance between the knee joint pivot axis 302 and the virtual lock axis 304, and θ is the hyperextension angle at the knee. Equation (1) takes advantage of the approximation sin θ≈θ, for small values of θ.

Users were able to distinctly notice hyperextension in earlier knee designs [Refs. 3-5], which had approximately 3° of hyperextension. We determined that less than about 1° of hyperextension is desired. The latch movement was measured to be about 5 mm in our prototype. Therefore, to achieve the goal of reduced hyperextension, we positioned the virtual lock axis 304 about 30 cm below the knee joint pivot axis 302. However, while a low virtual lock axis 304 can reduce hyperextension, it also means that a wider range of ground reaction forces 206 (transition points 900) are able to unlock the latch 402.

An axis can sometimes be implemented as either a physical axis or a virtual axis. Whereas a physical axis, such as the physical lock axis implemented in the LCKnee prosthetic knee joint by Andrysek [Ref. 17], typically uses fewer parts and may be more robust than a virtual axis, a virtual axis allows much more flexibility in placing a lock axis in a prosthesis, and a virtual axis can result in a more compact design. Since the desired location of the lock axis 304 is far from the knee joint pivot axis 302, we chose to implement the lock axis as a virtual axis, at least in part because a physical, single-axis implementation of the latch 402 would have been bulky.

As noted, the virtual lock axis 304 is implemented with a four-bar linkage 408. In the embodiment shown in FIGS. 4-7, the position of the virtual lock axis 304 is fixed. However, in other embodiments, the position of the virtual lock axis 304 is adjustable. In an embodiment shown in FIG. 10, a plate 1000 of the latch 402 defines a plurality of first holes, exemplified by first holes 1002, and 1004. One rotating joint 414 of the four-bar linkage 408 is attached to the plate 1000 via a selected one of the first holes 1002-1004. The plate 1000 may also define a plurality of second holes (not shown), and another rotating joint 416 of the four-bar linkage 408 may be attached to the plate 1000 via a selected one of the second holes.

By attaching one of the two rotating joints 414 or 416 via a selected one of the first holes 1002-1004, and optionally attaching the other of the two rotating joints 416 or 414 via a selected one of the second holes, the relative locations of the two rotating joints 414 or 416 may be set. Changing the location of one or both of the two rotating joints 414 and 416 changes the location of the virtual lock axis 304, which can alter stability and locking characteristics of the prosthesis.

For example, moving the virtual lock axis 304 up (as viewed in FIG. 10, i.e., towards the knee) and forward (towards the toe) decreases the area through which the ground reaction force 206 vector has to pass between the virtual lock axis 304 and the knee joint pivot axis 302, which makes the latch 402 more stable and more difficult to unlock. On the other hand, moving the virtual lock axis 304 down (towards the foot) and back (towards the heel) increases the area available for the ground reaction force 206 vector to disengage the latch 402, making the latch 402 easier to unlock.

Thus, a desired stability/ease of unlocking can be selected, by selecting one of the first holes 1002-1004 and one of the second holes. The number of combinations of first 1002-1004 and second holes defines a number of selectable stabilities/eases of unlocking combinations, thereby making the latch 402 discretely adjustable.

Figure 10:
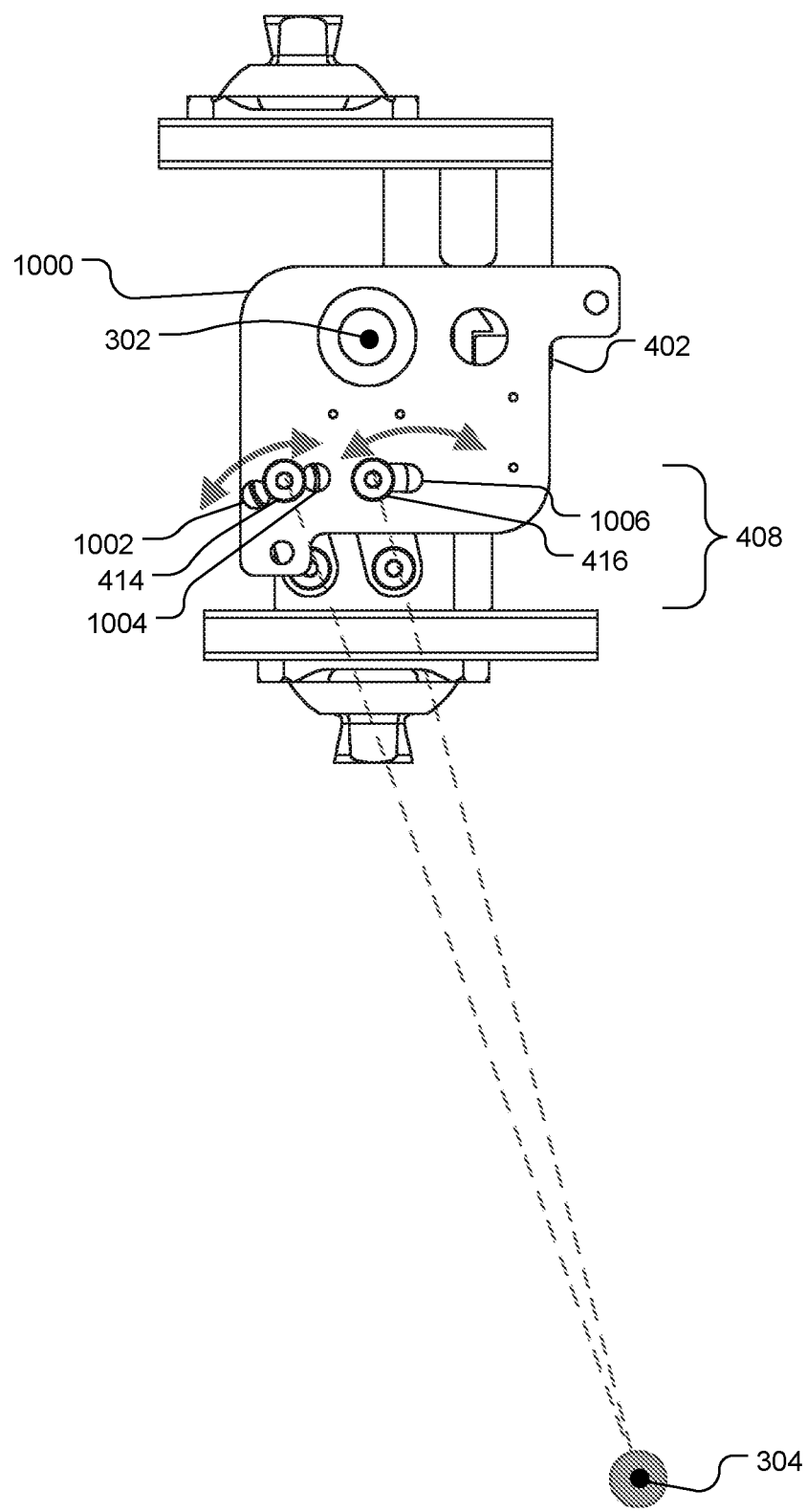
FIG. 10 is an illustration of an adjustable four-bar linkage, according to embodiments of the present invention.

In another embodiment shown in FIG. 10, the plate 1000 of the latch 402 defines an arc-shaped slot 1006, and one rotating joint 416 of the four-bar linkage 408 is attached to the plate 1000 via the arc-shaped slot 1006. The plate 1000 may also define a second arc-shaped slot (not shown), and the other rotating joint 414 may be attached to the plate 1000 via the second arc-shaped slot. With one or two arc-shaped slots, the location of one or both of the two rotating joints 414 and 416 may be infinitely adjusted, i.e., to any location accommodated by the respective arc-shaped slot. As with the holes 1002-1004, changing the relative locations of the two rotating joints 414 and 416 changes the location of the virtual lock axis 304.

In other embodiments, one of the two rotating joints 414 and 416 may be attached to the plate 1000 via a selected one of a plurality of holes, and the other one of the two rotating joints 414 and 416 may be attached to the plate 1000 via an arc-shaped slot. In yet other embodiments, one of the two rotating joints 414 and 416 may be attached to the plate 1000 via a single hole, and thereby not be adjustable, and the other one of the two rotating joints 414 and 416 may be attached to the plate 1000 via a selected one of a plurality of holes or an arc-shaped slot.

Structural Analysis of Latch Mechanism

Figure 11:
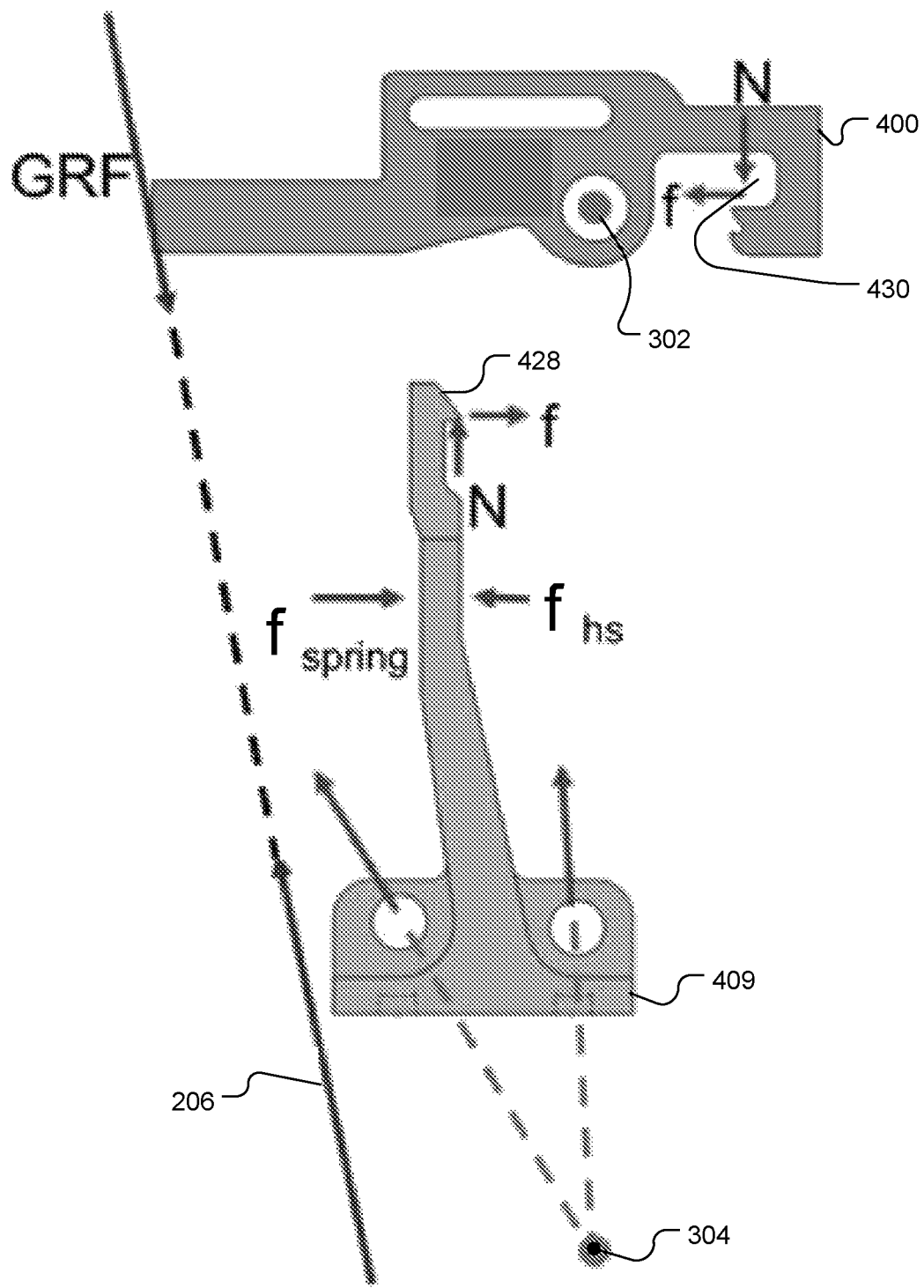
FIG. 11 is a free body diagram of relevant forces on components of the stance stability module of FIGS. 4-7 at heel strike, according to an embodiment of the present invention.

Structural integrity of the latching mechanism at heel strike is critical to keep the knee locked and prevent buckling. A free body diagram of relevant forces on the latch mechanism at heel strike is shown in FIG. 11. A sum of moments on the latch 402 about the virtual lock axis 304 symbolically represented by $\Sigma M_{LA}$, may be calculated according as follows:

$$\Sigma M_{LA} = GRF \cdot d_{GRF} + f_{spring} \cdot d_{spring} + f \cdot d_f + N \cdot d_n - f_{hs} \cdot d_{hs} \quad (2)$$

where $d_{GRF}$, $d_{spring}$, $d_f$, $d_n$ and $d_{hs}$ are lever arm lengths from the knee joint axis 302 of the respective forces. All forces on the latch 402 create a positive moment that helps keep the latch 402 in the locked position, other than the reaction force $f_{hs}$ from the hard stop 434 (FIG. 4), against which a shank of the hook 428 presses. This means that the only reason the latch 402 might unlock at this stage is structural failure at the tip, but beam bending and tensile strength calculations show that the latch tip can withstand the applied normal forces. To increase safety, the latch tip may be machined from Aluminum 7075, while the rest of the parts may be machined from more common Aluminum 6061 alloy, or injection molded in plastic. This analysis suggests that this design provides robust locking and successfully mitigates risk of buckling at heel strike.

It should be noted that the stance stability mechanism relies on mechanical engagement, not friction, to keep the knee locked. This addresses the main drawback of Arelekatti and Winter's previous design [Refs. 3-5], which relied on friction between the knee and latch pieces to keep the knee locked. Any issues related to lack of reliability or variability of friction forces, or with the knee unlocking under forces high enough to overcome friction, are not seen in the current design.

Early Stance Flexion Module

The development of the early stance flexion module 406 (FIG. 4) was a major focus of the design of this prosthesis. While prostheses designed for the developing world typically ignore early stance flexion, early stance flexion should be accommodated to a magnitude of about 20° to replicate able-bodied kinematics during the early stance 200 (FIG. 1) of walking gait 100, i.e., the about 20° bump 122 in the knee angle curve. Lack of early stance flexion is detrimental to users for several reasons, including: social stigma associated with conspicuous gait deviation from normal, long term health issues due to lack of cushioning provided after heel strike and over exertion at the hip to compensate for lack of such flexion.

Embodiments of the present invention build off previous work, such as by Narang, Arelekatti and Winter, such as by improving previous designs and increasing adjustability to achieve early stance flexion. While a previous design implemented perceived ideal parameters calculated through biomechanical analysis, embodiments of the present invention allow a wider range of adjustments in order to facilitate early stance flexion.

The early stance flexion module 406 (FIG. 4) includes an early stance flexion joint 440 configured to pivot about an early stance flexion axis 442. The early stance flexion joint 440 may be implemented with a steel pin or other suitable pivot joint. The early stance flexion axis 442 is distinct from the knee joint pivot axis 302 and the virtual lock axis 304. The early stance flexion axis 442 pivotally couples the upper leg 110 to the prosthetic knee joint 303 about the early stance flexion axis 442. Position of the early stance flexion axis 442 is adjustable, relative to position of the knee joint pivot axis 302. In addition, torsional stiffness, i.e., restoring elastic force, of the early stance flexion joint 440 is adjustable. The early stance flexion module 406 may be configured to apply an adjustable preload torque that must be overcome to pivot the early stance flexion joint 440 about the early stance flexion axis 442. A spring may be used to apply the preload torque.

For previously developed prostheses, the positioning and stiffness for the early stance flexion axis 442 were determined by looking at the changing ground reaction force 206 vector of an able-bodied subject over the gait cycle 100. Since the ground reaction force 206 changes direction over the gait cycle 100, it is possible to position a rotational axis such that the axis is torqued in one direction by the ground reaction force 206 at one point in the gait cycle 100, and torqued in the opposite direction at a later time in the gait cycle 100.

In order to accurately determine the proper position to locate this axis in order to get the desired transition point, the ground reaction force 206 profile must be accurately known. However, one of the largest sources of uncertainty in this process is the ground reaction force 206 profile of a transfemoral amputee. Due to variations among users in choice of prosthetic feet, previous prosthetic knee experience and general experience using a prosthetic limb, different users have developed different ground reaction force 206 profiles. This variability in the ground reaction force 206 profile makes it difficult to determine appropriate knee parameters, such as joint stiffness and axis placement, prior to testing. Adjustability of the early stance flexion module 406 solves this problem.

Embodiments of the present invention include features that enable adjusting several parameters. One such feature is the ability to change the location of the axis of rotation, in order to account for varying ground reaction force profiles from transfemoral amputees. Another feature is the ability to change the effective torsional stiffness of the axis of rotation in order to make it easier or harder for the knee to flex. Yet another feature is the ability to preload the spring within the early stance flexion module, in order to both eliminate backlash and determine a minimum desired force for flexion.

Early Stance Flexion Axis Position Adjustability

Figure 12:
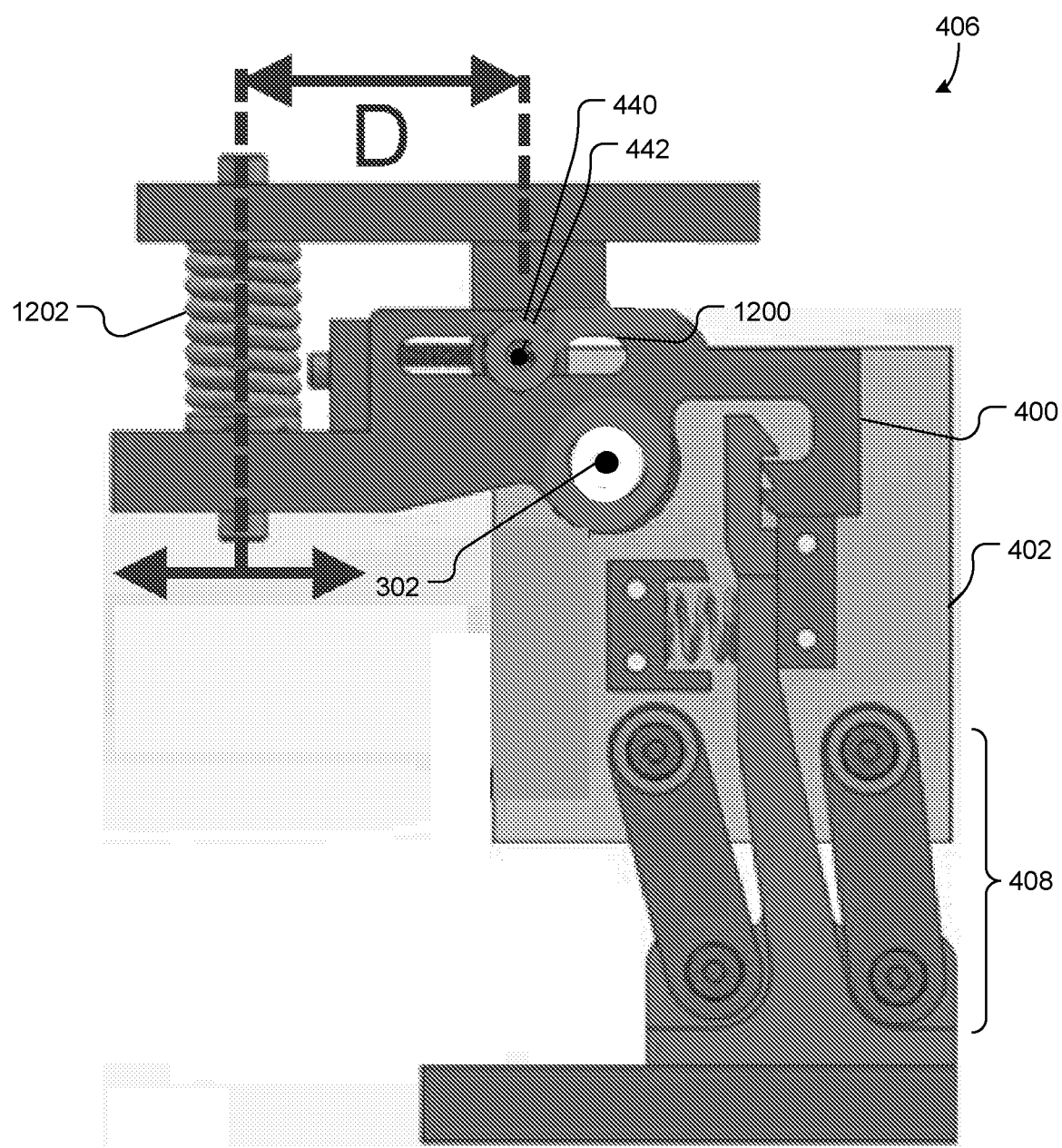
FIG. 12 is a side view illustration of the early stance flexion module of FIGS. 4-7, according to an embodiment of the present invention.
Figure 13:
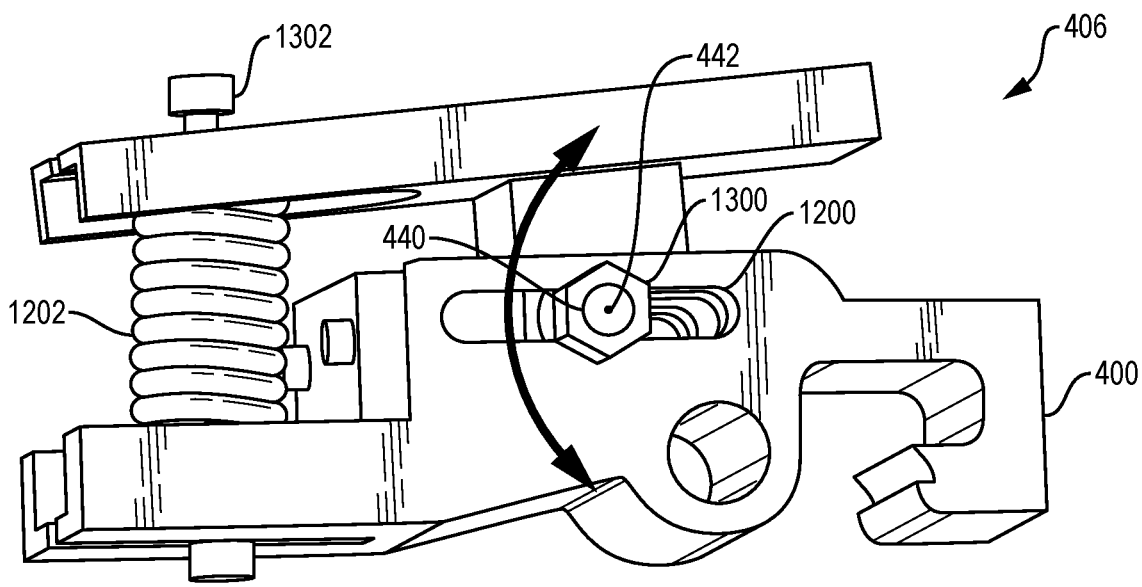
FIG. 13 is a slightly enlarged side view illustration of the early stance flexion module of FIGS. 4-7 and 12, according to an embodiment of the present invention.
Figure 14:
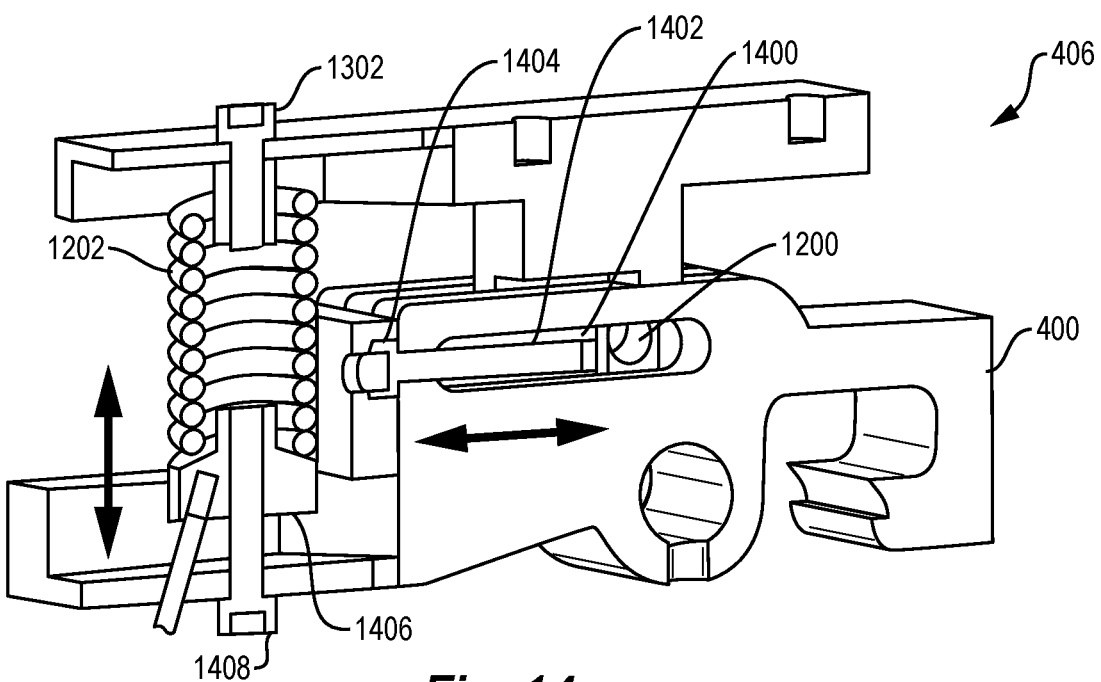
FIG. 14 is a cut-away side view illustration of the early stance flexion module of FIGS. 4-7, 12 and 13, according to an embodiment of the present invention.

The early stance flexion module 406 is shown slightly enlarged in FIG. 12, further enlarged in FIG. 13 and in cut-away in FIG. 14. The early stance flexion module 406 defines a slot 1300 that facilitates changing the position of the early stance flexion axis 442. In some embodiments, the slot is about 3.2 cm long. The axle of the early stance flexion joint 440 extends through the slot 1200 and through a similar slot (not visible) on the other side of the early stance flexion module 406. Axle nuts, exemplified by axle nut 1300 (FIG. 13), capture the axle and can be tightened to fix the axle at a desired location along the slot 1200. As can be seen in FIG. 14, the axle defines a transverse threaded hole 1400 in its center. A lead screw 1402 is threaded into the threaded hole 1400. An end cap 1404 of the screw 1402 is captured within a void. Thus, turning the screw 1402 moves the axle along the slot 1200. As noted, once the axle is in a desired location along the slot 1200, the axle nuts 1300 may be tightened to fix the axle in place.

The early stance flexion axis 442 should not be positioned further anterior than the knee joint pivot axis 302, otherwise the early stance flexion axis 442 may be constantly torqued in flexion, and the ground reaction force 206 may never pass anterior to the early stance flexion axis 442 in order to release the spring 1202 and allow straightening of the knee.

Early Stance Flexion Axis Torsional Stiffness Adjustability

Torsional stiffness of the early stance flexion axis 442 is caused by a compression spring (second spring) 1202 (FIG. 12) connected within the early stance flexion module 406 at a distance D from the early stance flexion axis 442. When the knee attempts to flex, the spring 1202 is compressed, as shown in FIG. 13. When the knee is locked for stance stability, the spring 1202 hits a hard stop 1302 to prevent hyperextension.

The torsional stiffness is, therefore, directly related to both the spring 1202 stiffness K and the distance D. Thus, the torsional stiffness may be adjusted by replacing the spring 1202 with another spring having a different stiffness K and/or by adjusting the distance D. In one embodiment, the slot 1200 allows D to be set within a range of about 2.4 cm to about 5.4 cm. This provides an approximately 2:1 range of the moment arm, and a commensurate range in the effective stiffness about the early stance flexion axis 442.

The spring 1202 may be easily replaced with another spring having a different stiffness K. The hard stop 1302 may be removably threaded into a preload stop 1406 (FIG. 14), and a screw 1408 may be removably threaded into the preload stop 1406, thereby facilitating disassembling the hard stop 1302, the preload stop 1406 and the screw 1408 for spring 1202 replacement. Replacements for the spring 1202 may have a wide range of stiffnesses K, thereby providing a wide range of effective early stance flexion axis 442 stiffnesses.

Choice of the spring 1202 may provide a coarse adjustment of the stiffness of the early stance flexion axis 442, and position of the early stance flexion axis 442 within the slot 1200 may provide a fine adjustment of the stiffness of the early stance flexion axis 442. In one embodiment, based on the range of compression springs used, the design was capable of reaching torsional stiffnesses in a range of about 0.8-7.0 Nm/kg-rad, well encompassing and going beyond the calculated ideal stiffness for the early stance flexion axis 442 by Narang and Winter (2.96 Nm/kg-rad [Ref. 1]).

Early Stance Flexion Axis Torsional Preload Spring

The spring 1202 may provide a preload torque to the early stance flexion axis 442, even when the knee is not bent. The preload stop 1406 has a wide conical surface, against which the spring 1202 bears. Adjusting the screw 1408 raises or lowers the preload stop 1406, thereby compressing or expanding the spring 1202, thereby varying the preload. This preload works to eliminate backlash that would otherwise be inherent in the design and was reported to be uncomfortable in past trials [Ref. 5]. Additionally, by preloading the spring 1202, a technician can set a specific threshold torque that must be applied to the knee by a user before the user overcomes the preload and the knee begins to flex in early stance 200. This is important because if the user begins to feel flexion at the beginning of early stance 200, the user may suspect that the knee is buckling, and the user may be overly cautious about applying her weight to the prosthetic knee. However, if the spring 1202 is preloaded, flexion is not felt immediately. The user perceives flexion only once she has applied her weight to the prosthesis.

Stance Stability Results

Figure 15:
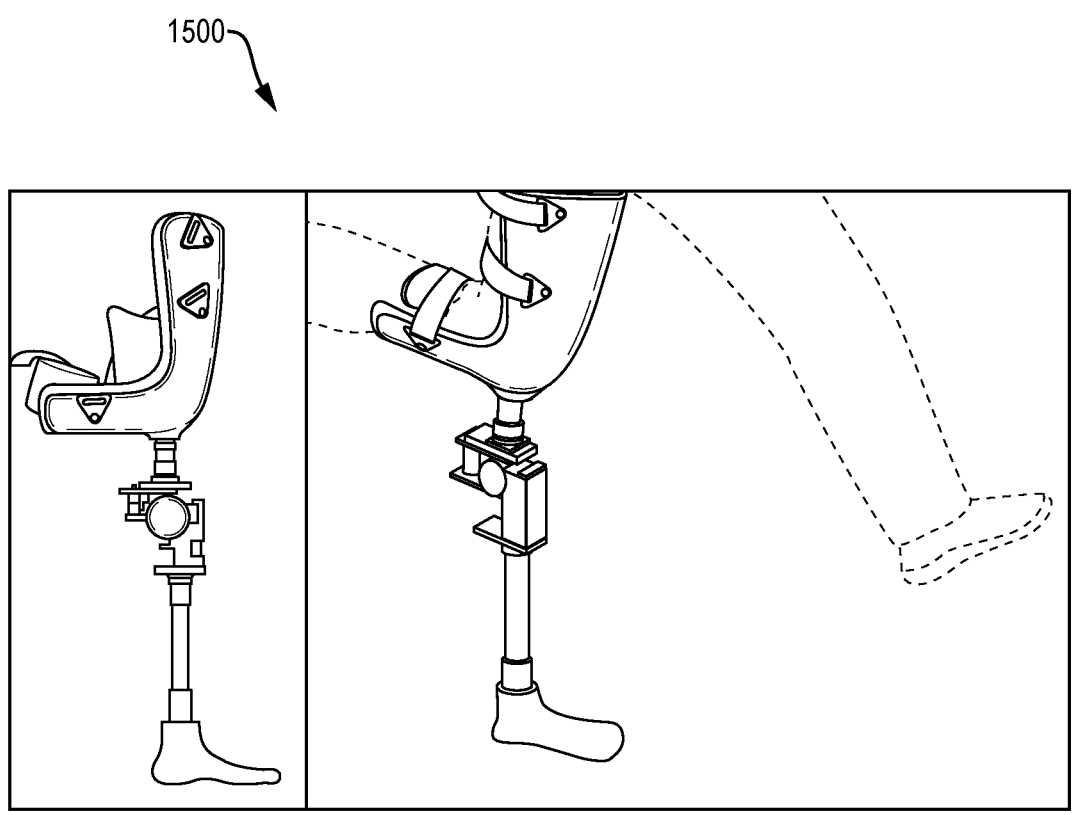
FIG. 15 is an illustration of a knee simulator being used to test a prototype prosthetic knee, according to an embodiment of the present invention.

After design and analysis of the stance stability module 300 and the early stance flexion module 406, metal parts for prototypes of both the latch 402 and the early stance flexion module 406 were CNC machined and assembled in our laboratory. A pylon and a passive prosthetic foot (Jaipur foot [Refs. 19, 20]) were attached to the lower leg 112, and the knee top was attached to a knee simulator 1500, to allow us to test the knee, as illustrated in FIG. 15.

Three of us used the knee simulator 1500 to qualitatively test the knee. Testers were able to walk normally without the knee buckling or failing to unlock. One tester was also able to walk with the knee at both slow and normal speeds over grass a distance of about 150 m (500 ft.) without issue. Qualitative feedback showed that testers felt stable on the knee and trusted putting their respective body weights on it more than during tests of prior art prosthetic knees [Refs. 5, 16].

Prior to testing on the ground, the locking mechanism for stance stability was tested by hand by rolling the foot over to simulate loads applied during a gait cycle 100. Various stiffness bias springs 436 (FIGS. 4-7) were tested, and it was observed that a bias spring (first spring) 436 with a stiffness constant greater than the calculated allowable range resulted in an inability to unlock the knee. On the other hand, for a spring 436 with a spring constant less than the allowable range, the knee would not reliably relock. This proved that the calculated range of spring constants was reasonable. Overall, a latching mechanism to provide stance stability was designed, prototyped and tested. Stance stability was emphasized as the most critical function of the knee prosthesis, and user testing and feedback showed that the prototype performed well, in terms of stance stability.

The prototype knee was tested only on flat surfaces, but the design and analysis suggest that the knee should function well on inclines, as the locking axis placement can be chosen such that the expected ground reaction forces 206 will unlock the knee at the appropriate time. The double latch's intermediate locking point 700 allows the knee to lock before reaching full extension, which is particularly advantageous for walking uphill.

Early Stance Flexion

A prototype early stance flexion module 406 is adjustable over a very broad range of functional parameters for achieving early stance 200 flexion. Using springs 1202 with stiffnesses up to about 175 N/mm, an axial stiffness exceeding 7 Nm/kg-rad was achieved, easily exceeding the previously calculated ideal stiffness of 2.96 Nm/kg-rad. Additionally, the early stance flexion axis 442 can be shifted by up to about 3.2 cm, and the maximum deflection achievable is over 22°. These parameters are highly dependent on the specific spring 1202 used, but because of the modularity of the system and the ability to easily replace spring 1202, the early stance flexion module 406 is capable of covering a broad range of stiffnesses, axial placements and preloads.

Swing Phase Control Module

The swing phase control module controls motion of the lower leg 112 during late stance 204 (FIG. 2) flexion and swing phase 106 (FIG. 1) flexion and extension. Narang [Ref. 1] identified a need for a damping system during the late stance 204 phase and the swing phase 106, since negative work is performed during these two phases of the gait cycle 100. Narang also developed a model, based on weight distribution of prostheses for transfemoral amputees, that identifies a moment needed about the knee joint pivot axis over the gait cycle 100, thus allowing him to identify a disparity in the amount of damping needed between flexion (during late stance 204 and early swing) and extension (during late swing). Approximately four times as much damping is needed during flexion as during the swing phase extension at normal gait speed [Ref. 1]. Previous work by Arelekatti and Winter [Refs. 3, 5] used this information to create a low-cost damping system that includes two dampers, i.e., a relatively large damper and a relatively small damper. Each damper includes a respective friction pad. The large damper is coupled via a one-way clutch. Thus, both friction dampers are engaged during flexion, while only the small damper is engaged during extension [Ref. 5].

Although the use of friction pads by Arelekatti and Winter in the earlier prototype is consistent with findings of Narang [Ref 1], relying on friction pads fails to meet the requirement for robustness and durability, as the friction pads wear over time and are susceptible to environmental contaminants, such as water and dust. More importantly, friction-based damping exhibits a stick-slip action, i.e. a non-zero torque is required to initiate motion to overcome static friction. All users in previous trials reported this stick-slip action to be undesirable [Ref. 5]. Additionally, friction pads offer a constant damping value, failing to accommodate changes in gait speed [Ref. 1]. The task for the swing phase control module is to improve upon the Arelekatti and Winter friction-based damping system by addressing these drawbacks, while keeping the system low-cost and robust.

Many damping alternatives to friction pad dampers were investigated. Pneumatic and hydraulic systems were considered for first and second order damping. Size limitations make pneumatic systems impractical choices for damping, due to the relatively high compressibility of air. We realized that a hydraulic damper would address these issues. Any of several linear or rotary hydraulic dampers may be used. On linear and several embodiments of a rotary hydraulic damper are described.

Damping System

Figure 16:
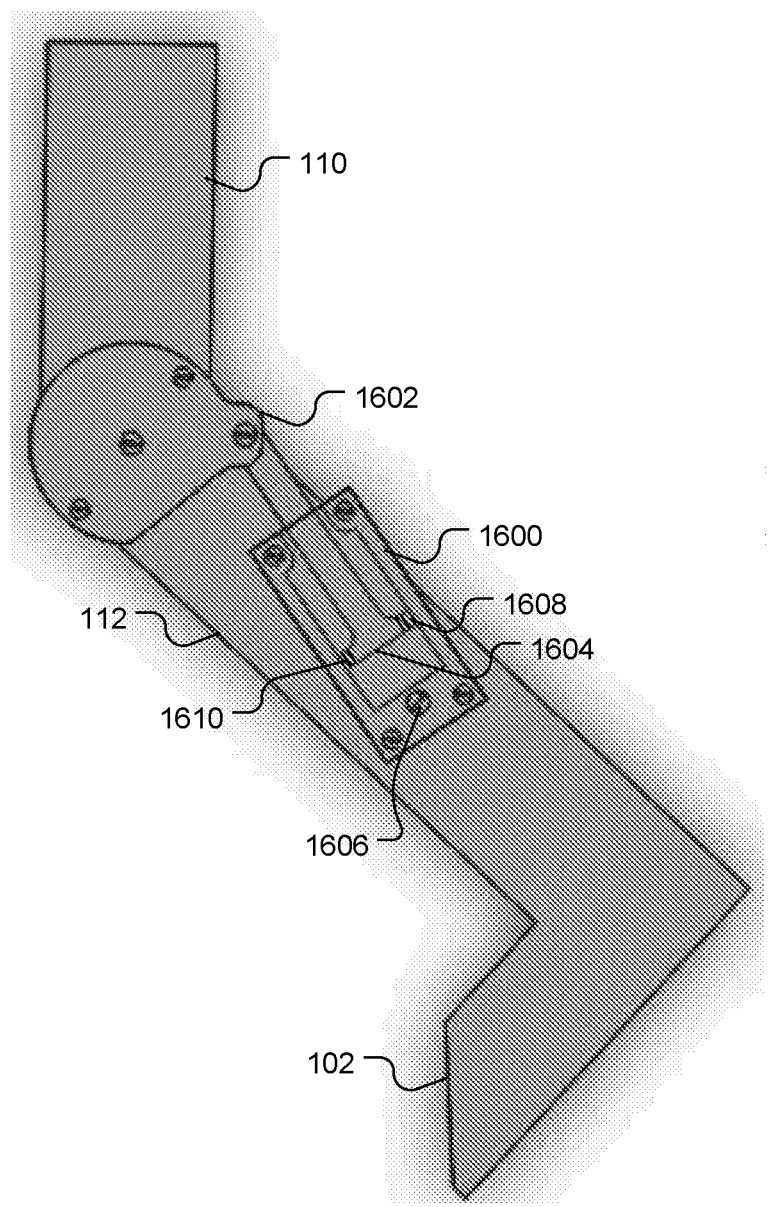
FIG. 16 is a schematic illustration of a piston-based linear hydraulic damper coupled to a prosthetic knee, according to an embodiment of the present invention.

Several damping models were created. The first model, schematically illustrated in FIG. 16, includes a linear hydraulic damper 1600 in a slider-crank arrangement. A first revolute joint 1602 of a piston 1604 is connected to the rotating knee part on the upper leg 110, and a bottom revolute joint 1606 of the piston 1604 is fixed to the lower leg 112. This linear damper 1600 model assumes bi-directional damping within the linear damper due to at least one one-way valve 1608 in the piston head. The piston head may also define a non-valved passage 1610 that meters (restricts in a predetermined way) flow of hydraulic fluid in both directions.

Thus, in a first direction of travel of the piston 1604, the hydraulic fluid may flow through only the valved passage 1608, whereas in the opposite direction of travel of the piston 1604, the hydraulic fluid may flow through both the valved 1608 and the non-valved 1610 passages. Consequently, the hydraulic fluid experiences more resistance to flow in the first direction than in the opposite direction. In other embodiments, both passages 1608 and 1610 have one-way valves installed antiparallel.

Figure 17:
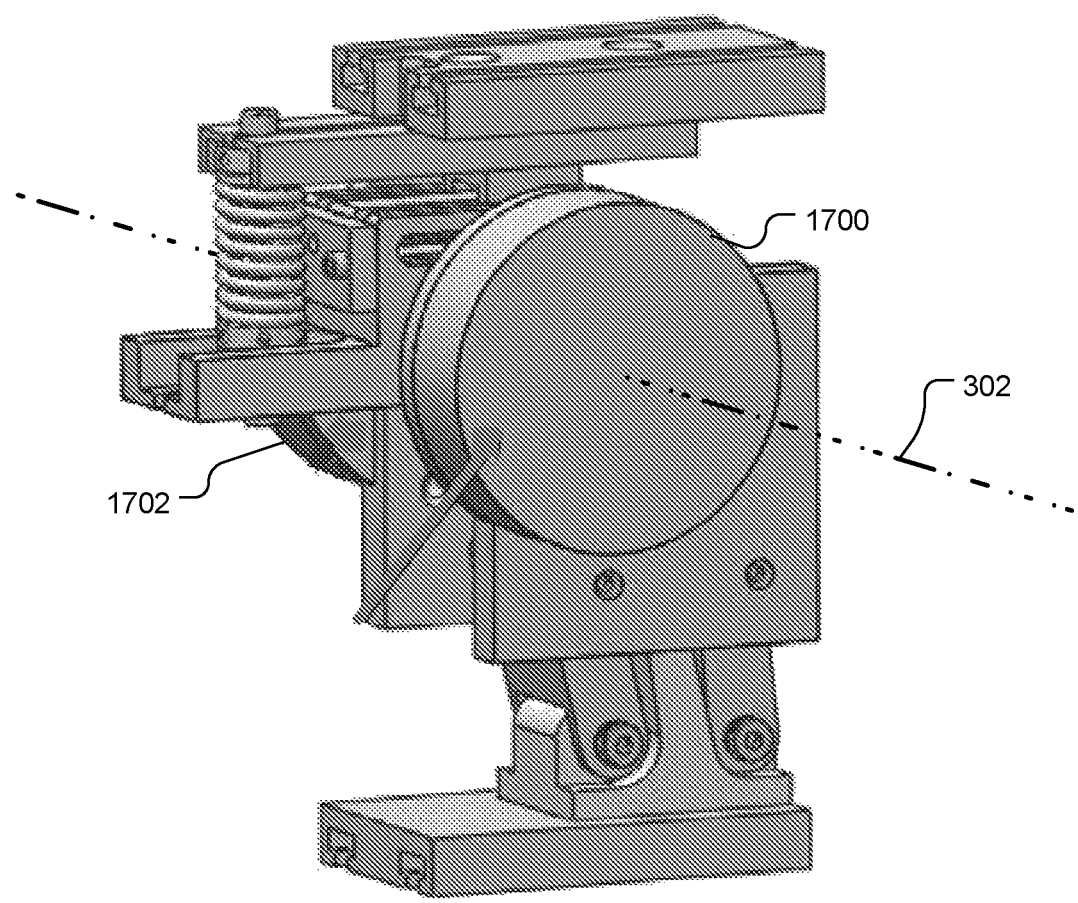
FIG. 17 is an illustration of two rotary hydraulic dampers coupled to a prosthetic knee, according to an embodiment of the present invention.

The second model, illustrated in FIG. 17, includes two rotary dampers 1700 and 1702 connected on opposite sides of the knee joint pivot axis 302. The two rotary dampers 1700 and 1702 may be mounted coaxially. At least one of the two rotary dampers 1700 and 1702 is mechanically coupled via a one-way roller clutch (not visible), although both of the rotary dampers 1700 and 1702 may be coupled via respective oppositely oriented one-way roller clutches. Similar to the previous design with friction pad dampers, these embodiments allow for one of the two rotary dampers 1700 or 1702 to be engaged during extension, and both of the rotary hydraulic dampers 1700 and 1702 to be engaged during flexion. If two oppositely oriented one-way clutches are used, one of the rotary hydraulic dampers 1700 or 1702 is engaged during extension, and the other rotary hydraulic damper 1702 or 1700 is engaged during flexion.

Alternatively, a directionally-dependent rotary hydraulic damper may be used for each rotary damper 1700 and 1702, eliminating the need for one-way clutches. An embodiment of such a directionally-dependent rotary hydraulic damper is described herein.

A MATLAB numerical computing environment (The MathWorks, Inc., Natick, Mass.) script was created to analyze how well these new damping systems and the previous friction pad damping system match the knee moment curve modeled by Narang [Refs. 1, 2], using able-bodied gait biomechanics, including knee angle and knee angular velocity [Ref 14]. From 0 to 40 percent of the gait cycle 100, i.e., during early stance 200 (FIG. 2), the ideal spring for early stance flexion identified by Narang was used [Ref. 1]. From 40 to 100 percent of the gait cycle 100, the damping system was engaged on the prosthesis.

In the friction damping system, the moment M is a constant value during flexion and a different constant value during extension, due to the differential damping system with friction pad dampers mounted on one-way roller clutches [Ref. 5].

For a linear viscous damper, such as the linear hydraulic damper 1600, the moment M created by a linear damper with a piston velocity v and a damping coefficient $b_l$ is:

$$M = b_l v^2 \tag{3}$$

A rotary damper design depends on a very viscous fluid between two rotating components and, therefore, the moment M created thereby depends on angular velocity $\omega$. The moment M created by a hydraulic rotary damper with angular velocity $\omega$ and rotary damping coefficient $b_r$ is the product of the damping coefficient and the angular velocity:

$$M = -b_r \omega \tag{4}$$

Figure 18:
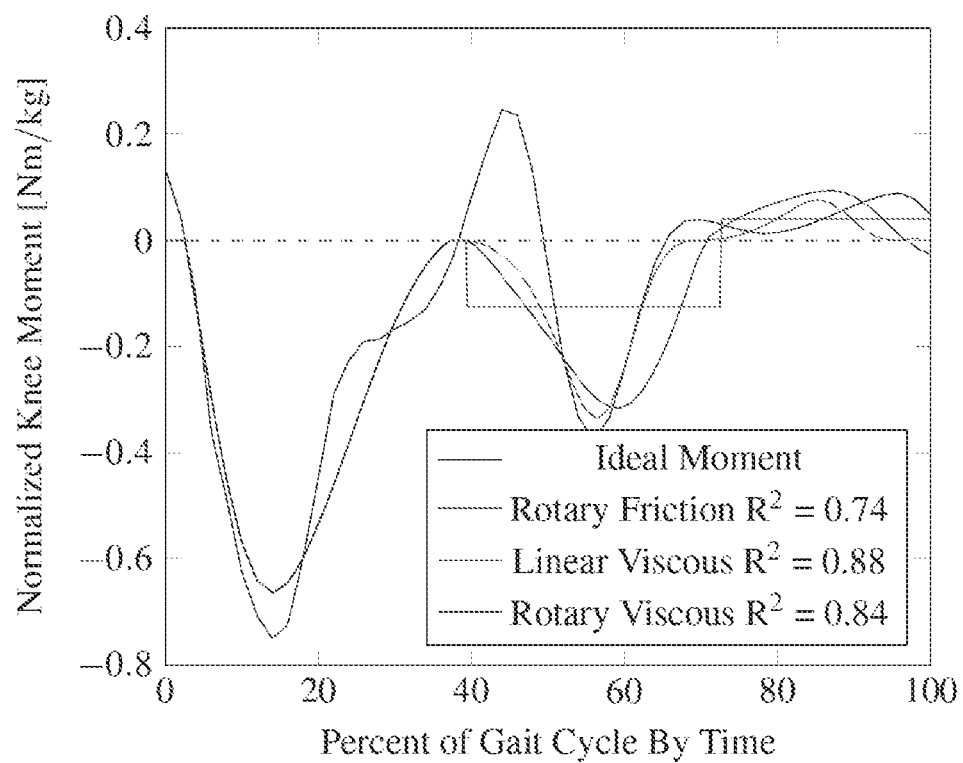
FIG. 18 is a graph that plots an ideal knee moment curve for a knee prosthesis as modeled in the prior art.

FIG. 18 is a graph that plots an ideal knee moment curve for a knee prosthesis as modeled by Narang [Ref. 1]. An ideal early stance flexion spring is incorporated between 0 and 40 percent of the gait cycle 100, and different damping systems of this study are engaged from 40 to 100 percent of the gait cycle 100. Correlation between the ideal moment profile and the moment profiles from these different damping systems was found by calculating $R^2$ (coefficient of determination) values. The $R^2$ values were 0.74, 0.88, and 0.84 for the friction pad dampers, linear hydraulic damper 1600 and the rotary hydraulic dampers 1700 and 1702, respectively. The $R^2$ values of the two hydraulic damping systems 1700 and 1702 were both greater than the $R^2$ value for the friction pad dampers, showing either rotary hydraulic damper would be an improvement to the previous design. Although the $R^2$ value of the linear hydraulic damper 1600 was greater than that of the rotary implementation 1700 and 1702, both designs were considered, and the benefits and drawbacks of each were analyzed. The rotary damper system 1700 and 1702 was eventually chosen, because of the advantages of simpler integration, less leakage due to the dynamic seal being a rotating one rather than a sliding one, and the simpler design of the damper, which does not need an accumulator or orifices, as would be required in the linear damper 1600.

Rotary Damper

Figure 19:
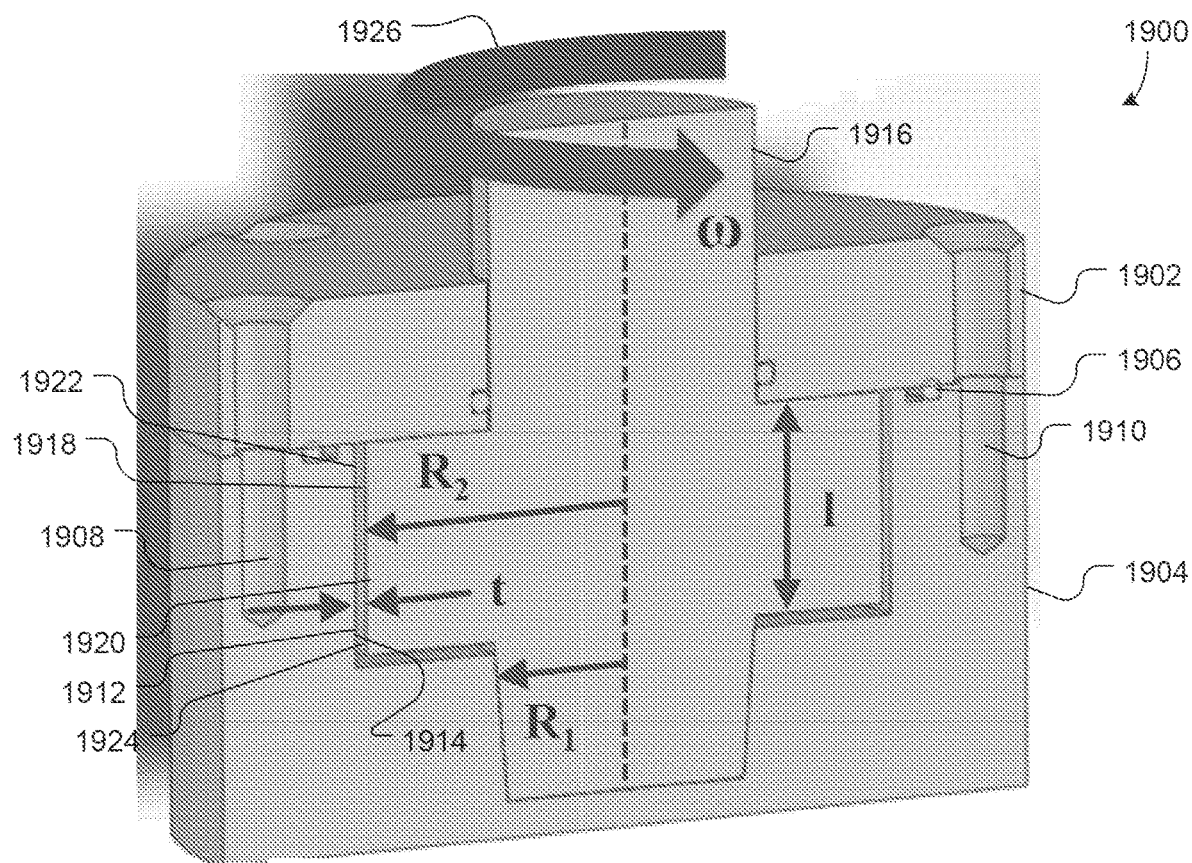
FIG. 19 is a cut-away view of a rotary hydraulic damper, according to an embodiment of the present invention.
Figure 20:
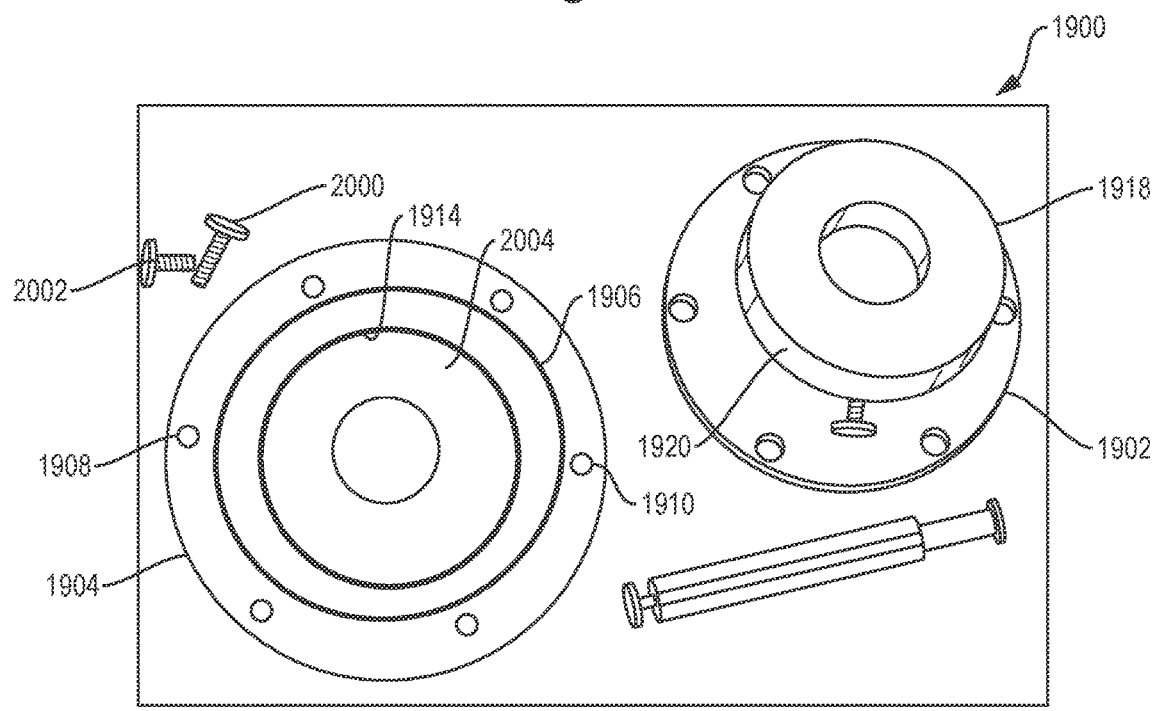
FIG. 20 is a top view of the rotary damper of FIG. 19, disassembled.

FIG. 19 is a cut-away view of a rotary hydraulic damper 1900, according to an embodiment of the present invention, and FIG. 20 is a top view of the rotary hydraulic damper 1900, disassembled. The rotary hydraulic damper 1900 includes top portion 1902 and a bottom portion 1904. A gasket 1906, such as a rubber o-ring, hydraulically seals the top portion 1902 to the bottom portion 1904. Screws, represented by screws 2000 and 2002 (FIG. 20) thread into holes, represented by holes 1908 and 1910, to assemble the top portion 1902 to the bottom portion 1904. Collectively, the top portion 1902 and the bottom portion 1904 define a cylinder 1912 that has an inner wall 1914. The inner wall defines a volume 2004 (best seen in FIG. 20).

An axle 1916 is longitudinally disposed within the cylinder 1912. The axle 1916 rotates within the cylinder 1912, relative to the cylinder. A rotor 1918 is mechanically coupled to the axle 1916 for rotation with the axle 1916. The rotor 1918 has an outer surface 1920 spaced apart from the inner wall 1914. A viscous hydraulic fluid 1922 is disposed within a volume 1924 defined between the inner wall 1914 of the cylinder 1912 and the outer surface 1920 of the rotor 1918.

The bottom portion 1904 may be made, such as milled, from Delrin or any suitable material. The rotor 1918 may be made, such as turned and milled, from Teflon-infused Delrin, for low friction, or any suitable material. The top portion 1902 may be made, such as laser cut, from an acrylic or any suitable material.

A small spring (not shown) at or below the bottom of the rotor 1918 may be used to urge the rotor 1918 against the top portion 1902. The rotor 1918 rotates, for example as indicated by arrow 1926, inside the stationary cylinder 1912, exerting a force on the viscous hydraulic fluid 1922 in the volume 1924, which causes a damping torque.

The rotary damper 1900 is governed by the following analytical relationship:

$$B_{viscous} = \frac{T}{\omega} = \frac{\pi\mu}{t}\left(2lR_2^3 + \left(\frac{R_2^4}{2} - \frac{R_1^4}{2}\right)\right) \quad (5)$$

where $B_{viscous}$ is the rotary damping coefficient, T is the damping torque, ω is rotational velocity and μ is viscosity of the hydraulic fluid 1922. Parameters $R_2$, $R_3$, l and t are labeled in FIG. 19. The relationship of Equation (5) was arrived at by summing viscous torque exerted by the relative rotation of concentric cylinders in a viscous medium and the torque due to an annular plate rotating on top of a fixed flat plate with a viscous medium in between [Ref. 21].

A prototype of the rotary hydraulic damper 1900 was assembled and tested with pure silicone oil (kinematic viscosity 1.0 m²/s), because silicone oil is one of the highest viscosity fluids available, and it is commonly used in hydraulic dampers of similar design. Using a flexural torque wrench, the torque required to rotate the damper 180° in a given time was measured. Thus, outputs of this test were torque and angular velocity, which were compared to expected torque values from Equation (5). The viscous hydraulic fluid 1922 has an important effect on the amount of damping this prototype could achieve.

Results

The torque values measured for the rotary hydraulic damper 1900 prototype were in the range of 3-5 Nm at moderate angular velocities between 3.14 and 6.28 rad/s (30 rpm to 60 rpm, a common range for walking gait), compared to an expected range of 2.67-3.04 Nm, respectively (Equation (5)). Due to shear thinning properties of silicone oil, the torque does not increase linearly with angular velocity. This is a necessary consideration in other embodiments of the rotary hydraulic damper 1900 in order to determine proper scaling relationships. Another consideration is that the maximum damping force required to match abled-bodied kinematics is up to 21 Nm at moderate angular velocities. Based on Equation (5), increased torque can be achieved by increasing the number and/or area of concentric circular walls, i.e., the inner wall 1914 of the cylinder 1912 and the outer surface 1920 of the rotor 1918, and/or by decreasing size of the gap (volume 1924) between the inner wall 1914 and the outer surface 1920, as is known in relation to commercial rotary hydraulic dampers.

As noted, two rotary hydraulic dampers 1900 may be mounted on the knee joint pivot axis 302, one rotary hydraulic damper 1900 engaged via a one-way roller clutch (not shown) to provide damping in flexion, and the other rotary hydraulic damper 1900 engaged on an opposite one-way clutch (not shown) to provide damping required during extension.

Parallel Disk Rotary Hydraulic Damper

Figure 21:
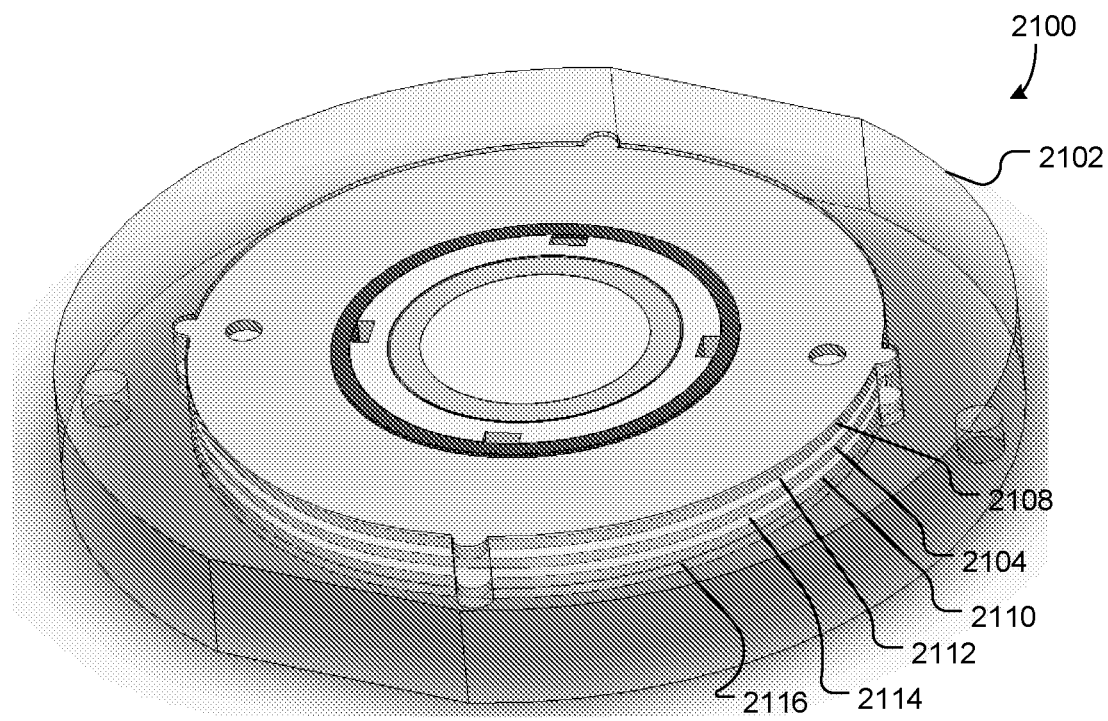
FIGS. 21 and 22 are respective isometric and cut-away isometric illustrations of a parallel disk rotary hydraulic damper, according to an embodiment of the present invention.
Figure 22:
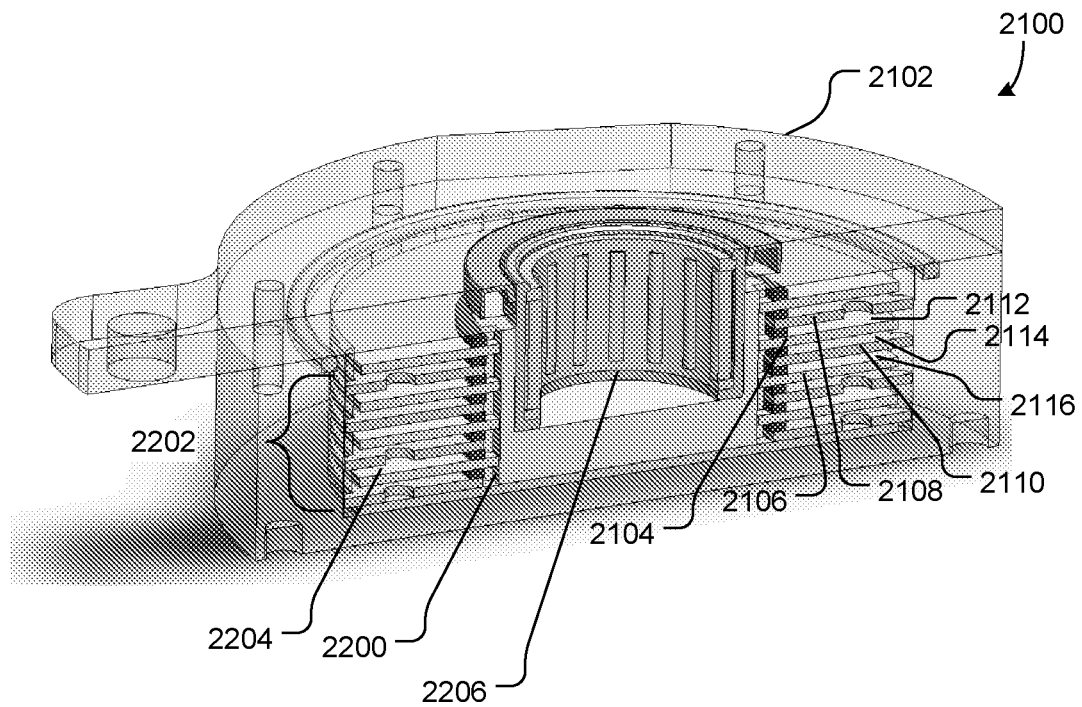

FIGS. 21 and 22 are respective isometric and cut-away isometric illustrations of a parallel disk rotary hydraulic damper 2100, according to an embodiment of the present invention. The parallel disk rotary hydraulic damper 2100 includes a housing 2102 and an axle 2200. The axle 2200 is longitudinally disposed within the housing 2102. The axle 2200 rotates within the housing 2102, relative to the housing.

A plurality of longitudinally spaced apart first plates, exemplified by plates 2104 and 2106, are mechanically coupled to the axle 2200 for rotation with the axle 2200. A plurality of second plates, exemplified by plates 2108 and 2110, are rigidly coupled to the housing 2102. The plurality of second plates 2108 and 2110 are interdigitated with the plurality of first plates 2104 and 2106, so as to define respective volumes, exemplified by volumes 2112, 2114 and 2116, between adjacent pairs of first and second plates, and collectively defining a total inter-plate volume 2202. A hydraulic fluid 2204 is disposed within the total inter-plate volume 2202. The axle 2200 is rigidly coupled to a one-way clutch 2206. Viscous torque is exerted on the plates 2104-2106 and 2108-2110 by the hydraulic fluid 2204, as a result of rotation of the first plates 2104-2106, relative to the second plates 2108-2110. Although the first and second plates 2104-2106 and 2108-2110 are flat in the embodiment shown in FIGS. 21 and 22, the plates need not be flat.

Directionally-Dependent Rotary Hydraulic Damper

Figure 23:
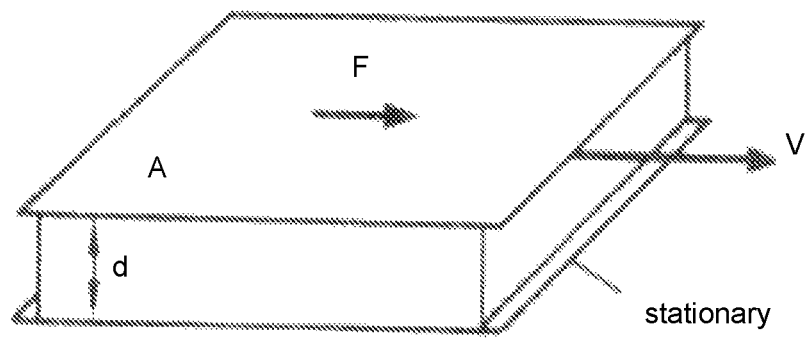
FIG. 23 is a schematic illustration of quantities involved in calculating shear force on a moving surface, relative to a stationary surface, with a hydraulic fluid therebetween, as known in the prior art.
Figure 24:
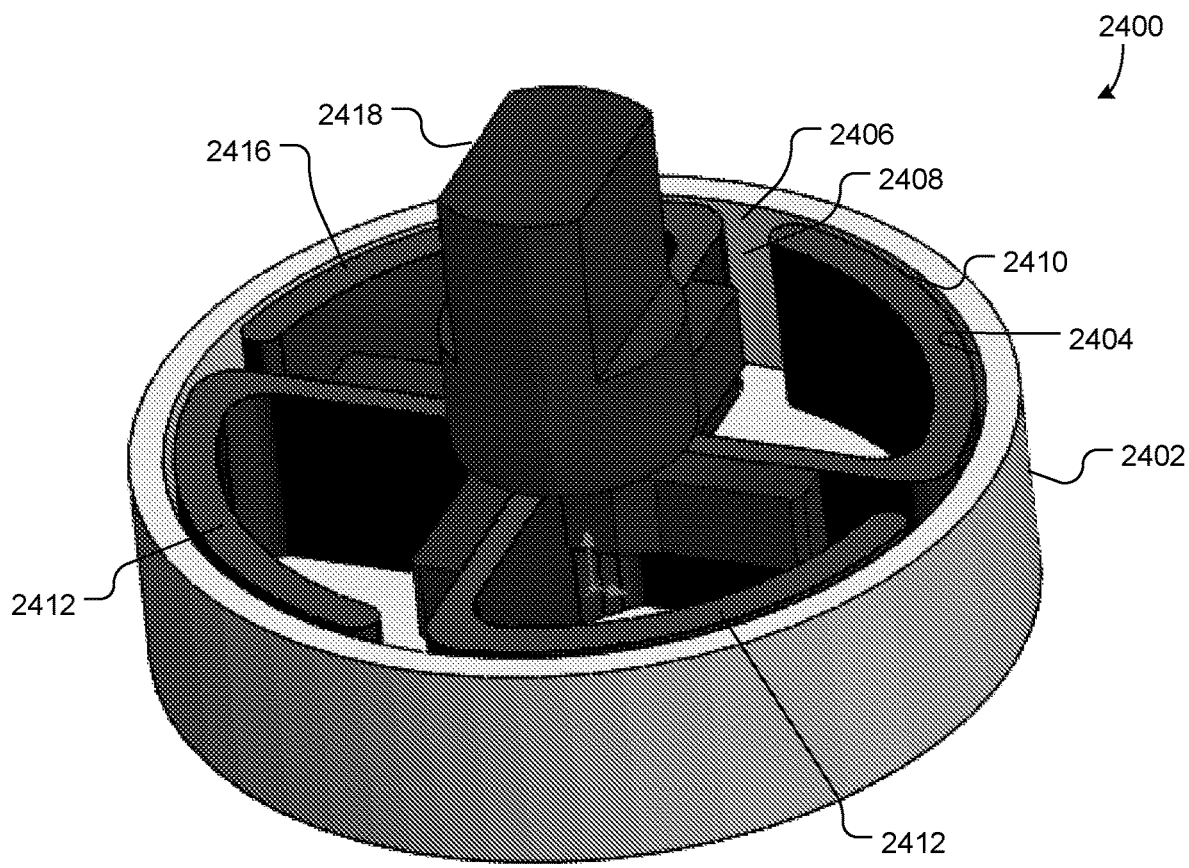
FIGS. 24 and 25 are respective isometric and top views of a directionally-dependent rotary hydraulic damper, according to an embodiment of the present invention.
Figure 25:
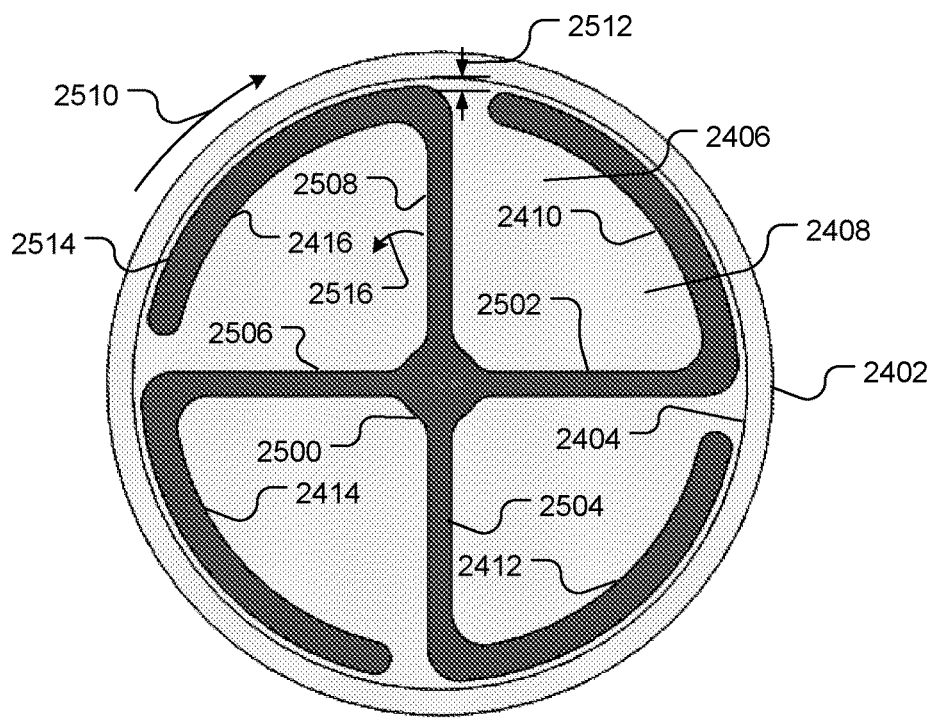

Many known rotary hydraulic dampers work due to fluid shearing between two walls. Shearing force is dependent on size of a gap between the two walls, wall area, fluid viscosity and velocity of shear, as governed by the following analytical relationship:

$$F = \frac{A\mu V}{d} \quad (6)$$

where A is wall area, μ is fluid viscosity, V is velocity of shear and d is gap size. FIG. 23 illustrates these quantities.

A directionally-dependent rotary hydraulic damper 2400 is described, with reference to FIGS. 24-30. The directionally-dependent rotary hydraulic damper 2400 includes a cylinder 2402 having an inner wall 2404. The inner wall 2404 defines a volume 2406. A hydraulic fluid 2408 is disposed within the volume 2406. An axle 2500 is longitudinally disposed within the cylinder 2402. The axle 2500 rotates within the cylinder 2402, relative to the cylinder.

At least one fin, exemplified by fins 2410, 2412, 2414 and 2416, is spaced apart from the inner wall 2404. The fins 2410-2416 are mechanically coupled to the axle 2500 by a spring. In the embodiment shown in FIGS. 24-27, each fin 2410-2116 is mechanically coupled to the axle 2500 by a respective spring 2502, 2504, 2506 and 2508. However, in other embodiments, more or fewer springs 2502-2508 than fins 2410-2416 may be used. For example, one spring may mechanically couple several fins to the axle 2500. In the embodiments shown in FIGS. 24-27, the fins 2410-2416 are mechanically coupled to the axle 2500 by the springs 2502-2508 for rotation with the axle 2500.

Figures 26, 27:
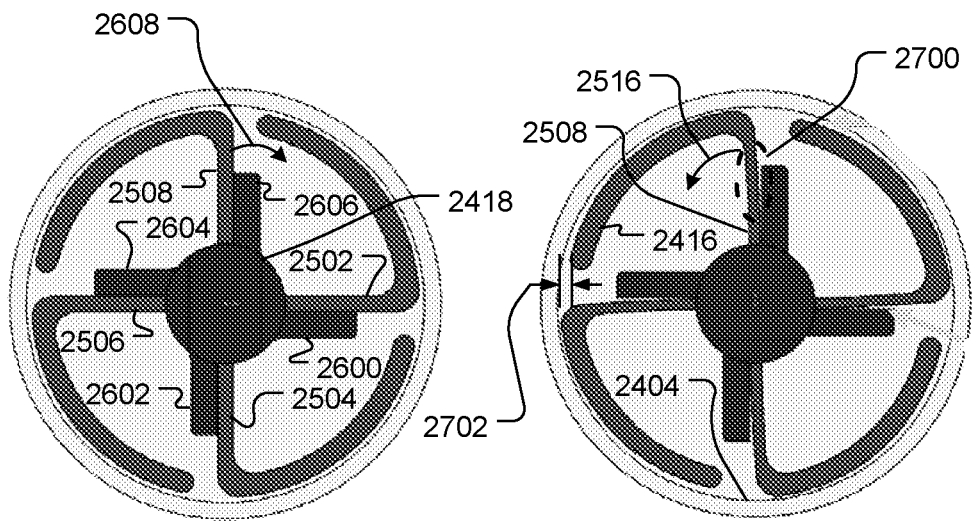
FIG. 26 is a top view of the directionally-dependent rotary hydraulic damper of FIGS. 24-25 illustrating a stop at least limiting deflection of springs when an axle rotates in one direction, according to an embodiment of the present invention.
FIG. 27 is a top view of the directionally-dependent rotary hydraulic damper of FIGS. 24-26 illustrating the stop allowing deflection of the springs when the axle rotates opposite the direction of FIG. 26, according to an embodiment of the present invention.

The fins 2410-2416 and the springs 2502-2508 are configured to deflect the springs 2502-2508 in response to a shear force of the hydraulic fluid 2408, between the fins 2410-2416 and the inner wall 2404, as a result of rotation of the axle 2500 in a first direction 2510. This deflection of the springs 2502-2508 moves the fins 2410-2416 away from the inner wall 2404, hereby increase spacing 2512 between the fins 2410-2416 and the inner wall 2404. For example, as the axle 2500 rotates in the first direction 2510 (FIG. 25), shear force of the hydraulic fluid 2408 between the fin 2416 and the inner wall 2404 in the gap 2514 inhibits rotation of the fin 2416 and bends the spring 2508 in a direction indicated by arrow 2516. This bending is shown in FIG. 27 (see portion of spring 2508 within dashed line 2700). The bending 2700 of the spring 2508 causes the fin 2416 to withdraw from the inner wall 2404, increasing the size of the gap 2702 between the fin 2416 and the inner wall 2404. Increasing the gap 2702 reduces the shear force, making rotation of the axle 2500 easier.

Figures 28, 29:
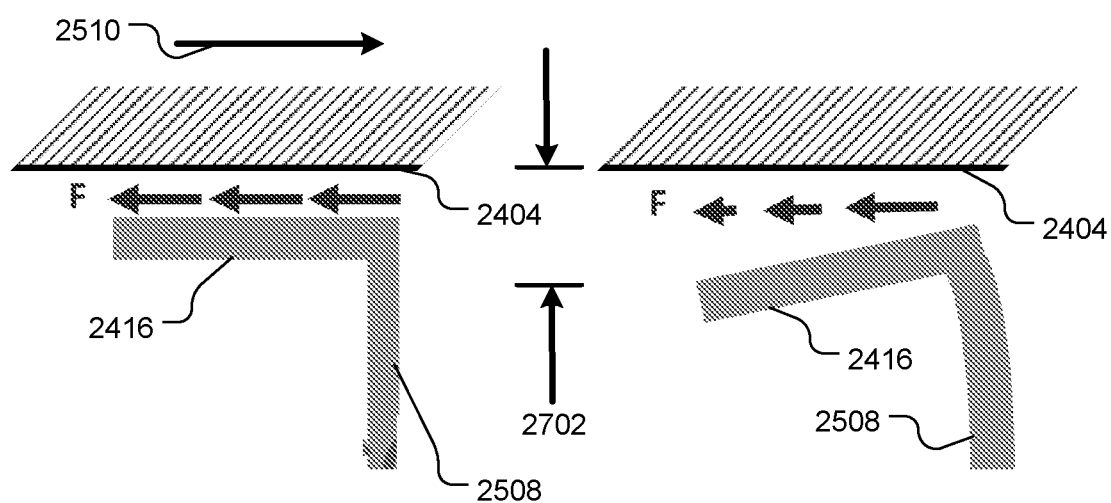
FIG. 28 is a schematic illustration of a fin of the directionally-dependent rotary hydraulic damper of FIGS. 24-27 showing a shear force on the fin when the axle rotates in the direction of FIG. 26, according to an embodiment of the present invention.
FIG. 29 is a schematic illustration of the fin of FIG. 28 showing a shear force on the fin when the axle rotates in the direction of FIG. 27, and showing consequential deflection of a corresponding spring, according to an embodiment of the present invention.
Figure 30:
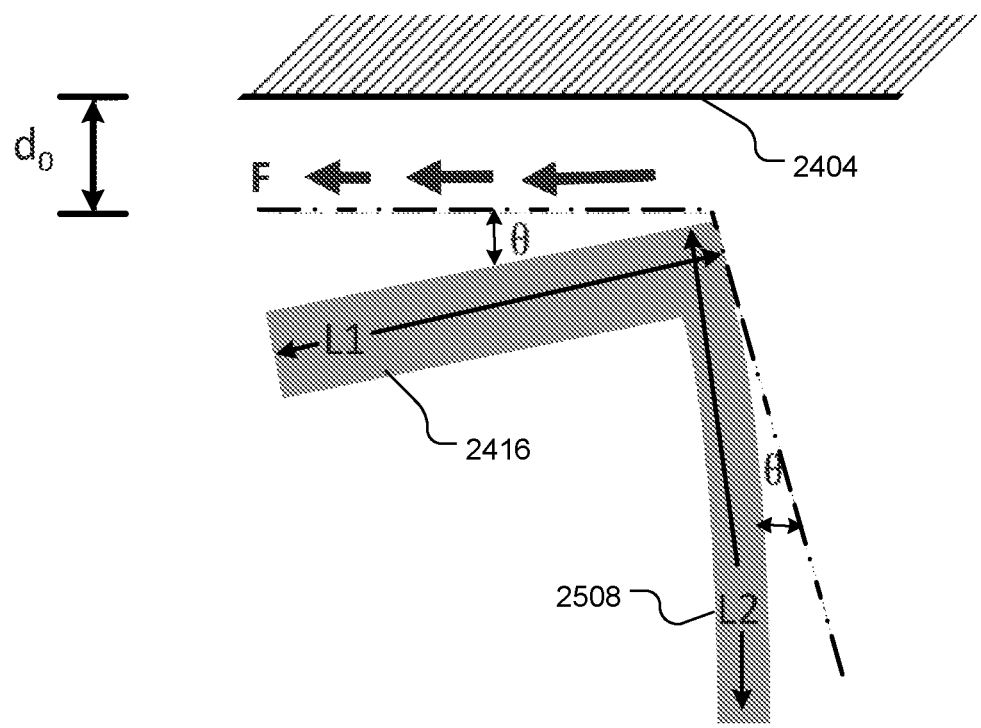
FIG. 30 is similar to FIG. 29, annotated with dimensions used in analyzing the shear force, according to an embodiment of the present invention.

FIG. 28 is a schematic illustration of one fin 2416. As the fin 2416 rotates in the direction 2510, relative to the inner wall 2404, the hydraulic fluid 2408 creates a shear force F on the fin 2416, which bends the spring 2508, as shown schematically in FIG. 29. The bending of the spring 2508 displaces the fin 2416 from the inner wall 2404, increasing the gap 2702, thereby reducing the shear force F on the fin 2416.

Returning to FIG. 24, the directionally-dependent rotary hydraulic damper 2400 also includes a stop 2418 configured to at least limit, and in some embodiments prevent, deflection of the springs 2502-2508 when the axle 2500 rotates in a direction opposite the first direction 2510. In the embodiment shown in FIGS. 24-27, as can be seen most clearly in FIG. 26, the stop 2418 includes four rigid wings 2600, 2602, 2604 and 2606. Each wing 2600-2606 corresponds to one of the springs 2502-2508. Each wing 2600-2606 is sized and positioned against one side of its respective spring 2502-2508, so as to prevent, or at least limit, deflection of the respective spring 2502-2508 in a direction indicated by arrow 2608.

Consequently, rotating the axle 2500 in a direction opposite the first direction 2510 (FIG. 25) does not reduce the shear force on the fins 2410-2416. Thus, when the axle 2500 rotates opposite the first direction 2510 (FIG. 25), the axle 2500 experiences more damping than when the axle 2500 rotates in the first direction 2510. Forces involved can be analyzed using FIG. 30, which is similar to FIG. 29, but annotated with dimensions. Using a cantilever beam equation, θ can be found as a function of the shear forces applied:

$$\theta = \frac{F \times L_2^2}{2 \times E \times I_2} \quad (7)$$

Shear forces can be calculated as a function of deflection θ:

$$F = \frac{b \times \omega \times \mu \times L_1}{d_0 + \frac{L_2}{2}\sin\theta} \quad (8)$$

The two Equations (7) and (8) are coupled, so MATLAB numerical computing environment or another tool may be used to find an analytical solution. Input parameters for one such computation are summarized in Table 1, and results are summarized in Table 2.

TABLE 1

| Input Parameters | |
| --- | --- |
| Beam width | 0.0015; % [m] |
| Depth (out of the page) | 0.0254; % [m] |
| $L_1$ | 0.025; % [m] |
| $d_0$ | 0.0005; % [m] |
| r | $L_1 + h + d_0$; % [m] |
| $L_2$ | $2\pi r/a - 0.002$; % [m] |
| ω | 3; % [rad/sec] |
| E | 70E9; % [Pa] for aluminum |
| I | b*(h^3)/12; % [m^4] |
| μ | 1000; % [kg/(m*s)] |

TABLE 2

| Results | |
| --- | --- |
| Angular deflection | 2.3° |
| Torque in direction 1 | 18.0 Nm |
| Torque in direction 2 | 6.9 Nm |

For reasonable dimensions and viscosity values, torques within the expected range were observed. A model was 3D printed and tested using lower viscosity fluid, and torques within the expected range were observed.

Figure 31:
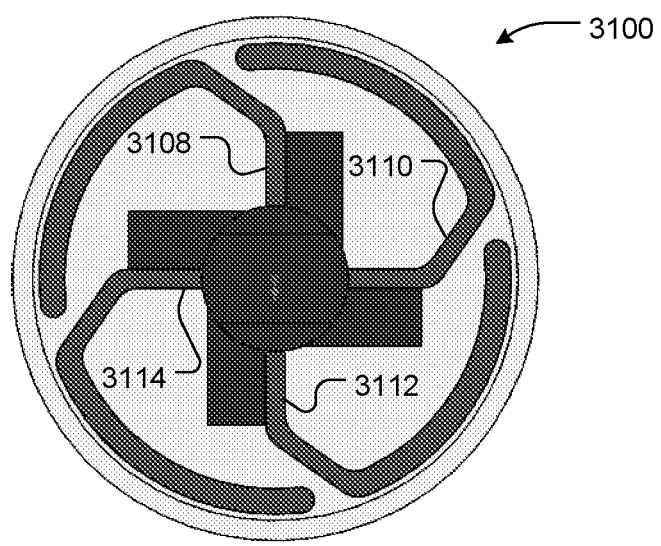
FIG. 31 is a top view of a directionally-dependent rotary hydraulic damper according to another embodiment of the present invention.

FIG. 31 is a top view of a directionally-dependent rotary hydraulic damper 3100 according to another embodiment of the present invention. As can be seen in FIG. 31, the springs 3108, 3110, 3112 and 3114 need not be straight or radially directed away from the axle 2500.

Swing Extension Energy Storage Module

Figure 32:
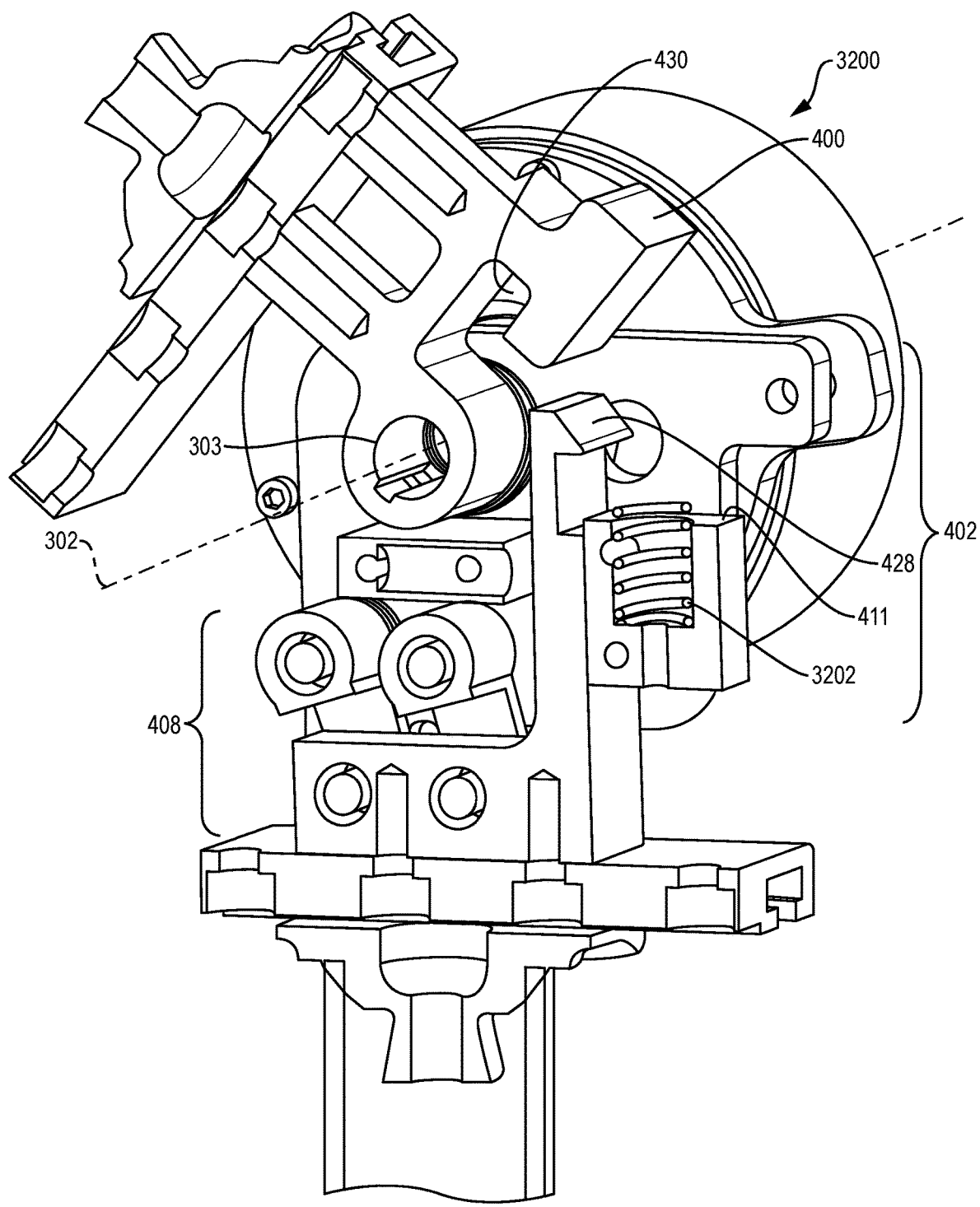
FIG. 32 is a cut-away illustration of a prosthetic knee, and specifically a swing extension energy storage module of the prosthetic knee, with the knee bent, according to an embodiment of the present invention.
Figure 33:
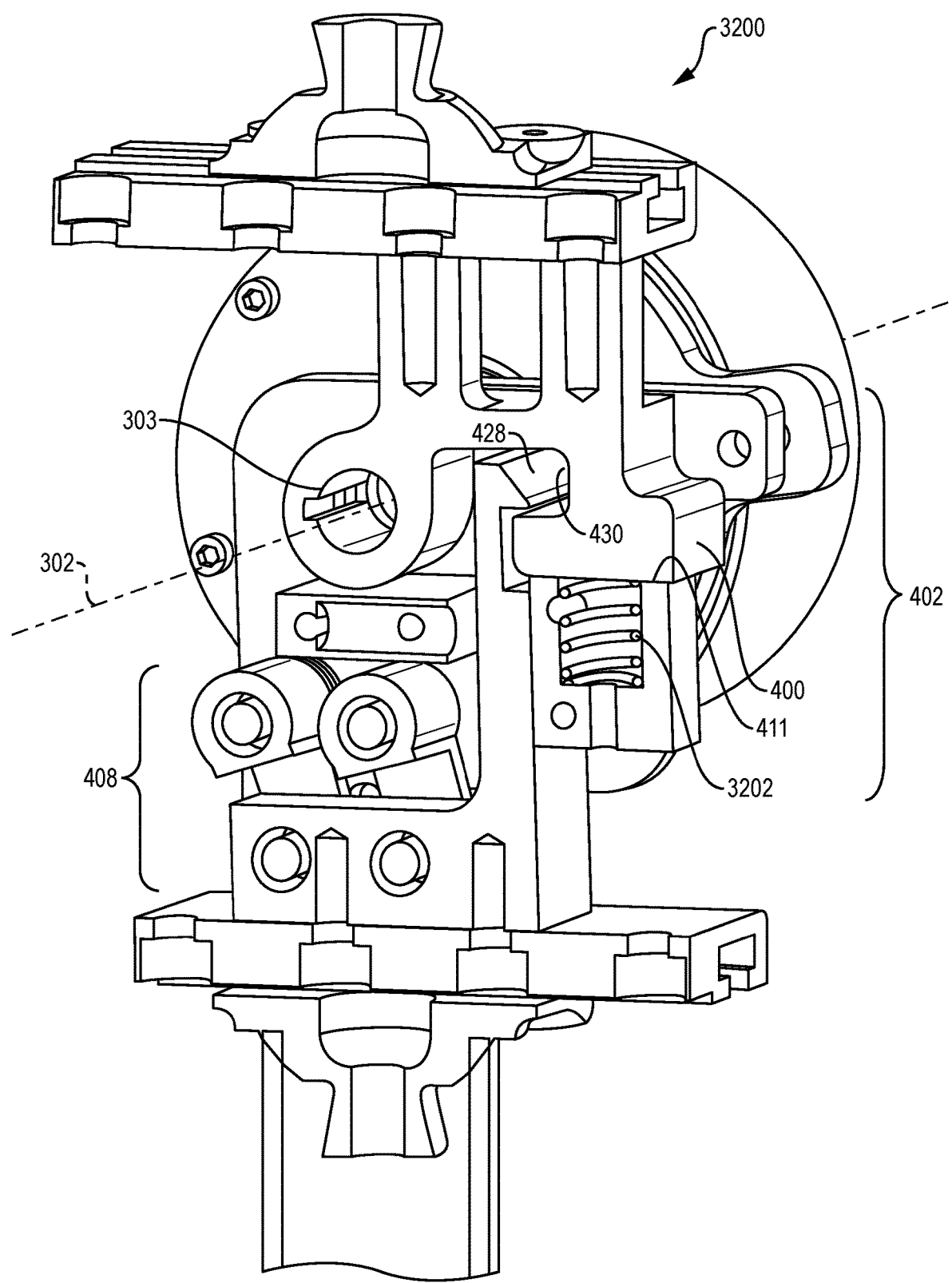
FIG. 33 is a cut-away illustration of the prosthetic knee of FIG. 32, with the knee straight and locked, according to an embodiment of the present invention.

FIGS. 32 and 33 are cut-away illustrations of a prosthetic knee, and specifically a swing extension energy storage module 3200 of the prosthetic knee, according to an embodiment of the present invention. FIG. 32 shows the knee bent, and FIG. 33 shows the knee straight and locked. As noted, the knee piece 400 is pivotally coupled to the latch 402 and pivots on the prosthetic knee joint 303, about the knee joint pivot axis 302. When the knee is straight and locked, as in FIG. 33, the hook 428 is engaged with the first notch 430, and the knee piece 400 presses against the first hard stop 411.

The swing extension energy storage module 3200 includes a spring 3202 (third spring). The spring 3202 is configured to deflect (compress, in the embodiment of FIGS. 32 and 33, although in other embodiments, the spring may expand or twist) in response to pivoting of the prosthetic knee joint 303. The spring 3202 deflects to store energy as the prosthetic knee straightens and/or locks, and the spring releases the stored energy as the knee unlocks and begins to bend.

The spring 3202 is deflected (compressed in FIG. 33) when the first notch 430 is engaged by the hook 428. When deflected, the spring 3202 urges the knee piece 400 away from the locked position, and therefore the spring 3202 urges the prosthetic knee joint to pivot about the knee joint pivot axis 302 so as to increase knee flexion angle of the prosthetic knee joint.

Discussion

A pressing social and physiological need for high performance, low-cost prosthetic devices in the developing world is evident. Described herein is a new passive prosthetic knee that enables able-bodied gait and high metabolic efficiency in transfemoral amputees.

The early stance flexion module 406 enables able-bodied gait during stance. The latch 402 ensures stance stability. Hydraulic fluid dampers 1600, 1900, 2100, 2400 or 3100 ensure reliable swing phase control. The swing extension energy storage module 3200 stores and returns energy as the knee locks and unlocks, respectively. These modules have been designed to work together to enable able-bodied gait over the entire gait cycle 100. However, each of these modules may be used individually or in any combination.

REFERENCES

[Ref. 1] Narang, Y. S., Arelekatti, V. M., and Winter, A. G., 2016. "The effects of the inertial properties of above-knee prostheses on optimal stiffness, damping, and engagement parameters of passive prosthetic knees." Journal of Biomechanical Engineering, 138(12), p. 121002.

[Ref. 2] Narang, Y. S., Arelekatti, V. M., and Winter, A. G., 2016. "The effects of prosthesis inertial properties on prosthetic knee moment and hip energetics required to achieve able-bodied kinematics." IEEE Transactions on Neural Systems and Rehabilitation Engineering, 24(7), pp. 754-763.

[Ref. 3] Arelekatti, V. N. M., and Winter V, A. G., 2016. "Design of a fully passive prosthetic knee mechanism for transfemoral amputees in India." Journal of Mechanisms and Robotics.

[Ref. 4] Arelekatti, V. M., and Winter, A. G., 2015. "Design of mechanism and preliminary field validation of low-cost, passive prosthetic knee for users with transfemoral amputation in India." In ASME 2015 International Design Engineering Technical Conferences and Computers and Information in Engineering Conference, American Society of Mechanical Engineers, pp. V05AT08A043-V05AT08A043.

[Ref. 5] Arelekatti, V. M., and Winter, A. G., "Design of a fully passive prosthetic knee mechanism for transfemoral amputees in India." In Rehabilitation Robotics (ICORR), 2015 IEEE International Conference on, IEEE, pp. 350-356.

[Ref. 6] Narang, I. C., Mathur, B. P., Singh, P., and Jape, V. S., 1984. "Functional capabilities of lower limb amputees." Prosthetics and Orthotics International, 8(1), April, pp. 43-51.

[Ref. 7] Narang, Y. S., "Identification of Design Requirements for a High-Performance, Low-Cost, Passive Prosthetic Knee Through User Analysis and Dynamic Simulation." Master's thesis, Massachusetts Institute of Technology, Cambridge Mass., May, 2013.

[Ref. 8] Narang, Y., Austin-Breneman, J., Arelekatti, V. N. M., and Winter, A., 2016. "Using biomechanical and human-centered analysis to determine design requirements for a prosthetic knee for use in India."

[Ref. 9] Rybarczyk, B., Nyenhuis, D. L., Nicholas, J. J., Cash, S. M., and Kaiser, J., 1995. "Body image, perceived social stigma, and the prediction of psychosocial adjustment to leg amputation." Rehabilitation Psychology, 40(2), p. 95.

[Ref. 10] Horgan, O., and MacLachlan, M., 2004. "Psychosocial adjustment to lower-limb amputation: a review." Disability and Rehabilitation, 20(14-15), pp. 837-850.

[Ref. 11] Mohan, D., 1967. "A Report on Amputees in India."

[Ref. 12] Hamner, S. R., Narayan, V. G., and Donaldson, K. M., 2013. "Designing for Scale: Development of the ReMotion Knee for Global Emerging Markets." Annals of Biomedical Engineering, 41(9), September, pp. 1851-9.

[Ref. 13] Wyss, D., Lindsay, S., Cleghorn, W. L., and Andrysek, J., 2013. "Priorities in lower limb prosthetic service delivery based on an international survey of prosthetists in low- and high-income countries." Prosthetics and orthotics international, December

[Ref. 14] Winter, D. A., 2009. Biomechanics and Motor Control of Human Movement, 4th ed. John Wiley & Sons, Inc.

[Ref. 15] Andrysek, J., 2010. "Lower-limb prosthetic technologies in the developing world: a review of literature from 1994-2010." Prosthetics and Orthotics International, 34(4), pp. 378-398.

[Ref. 16] Hamner, S. R., Narayan, V. G., and Donaldson, K. M., 2013. "Designing for Scale: Development of the ReMotion Knee for Global Emerging Markets." Annals of Biomedical Engineering, 41(9), September, pp. 1851-9.

[Ref. 17] Andrysek, J., Klejman, S., Torres-Moreno, R., Heim, W., Steinnagel, B., and Glasford, S., 2011. "Mobility function of a prosthetic knee joint with an automatic stance phase lock." Prosthetics and Orthotics International, 35(2), pp. 163-70.

[Ref. 18] Wyss, D., 2012. "Evaluation and design of a globally applicable rear-locking prosthetic knee mechanism." PhD thesis, University of Toronto.

[Ref. 19] Bhagwan Mahaveer Viklang Sahayata Samiti, 2014. What We Do: Above Knee Prosthesis. http://jaipur-foot.org/

[Ref. 20] Sharp, M., 1994. "The Jaipur limb and foot." Medicine and War, Vol. 10, Issue 3, pp. 207-211.

[Ref. 21] Kundu, P. K., Cohen, I. M., and Dowling, D. R., 2015. Fluid Mechanics. Academic Press.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented with appropriate levers, pivots, bars, pins, latches, springs, other flexures, etc., or combinations thereof.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

What is claimed is:

1. A prosthetic knee for mechanically coupling an upper leg to a lower leg that, in use, are subject to a ground reaction force acting through a center of pressure on a foot attached to the lower leg, such that orientation of the ground reaction force varies in space as a result of a gait, the prosthetic knee comprising:
   a prosthetic knee joint configured to couple to the upper leg and pivot about a knee joint pivot axis;
   a latch configured to couple to the lower leg and pivot about a virtual lock axis distinct from the knee joint pivot axis; and
   a linkage mechanically coupled to the latch, the linkage comprising at least two pivotable elements disposed along distinct axes, an intersection of the axes defining the virtual lock axis at a location off of the prosthetic knee and positioned such that the ground reaction force is posterior to the virtual lock axis in an early stance phase of the gait and the ground reaction force is anterior to the virtual lock axis in a late stance phase of the gait; wherein:
      the latch comprises a hook and defines a first notch that is engagable by the hook such that, when the first notch is engaged by the hook, the latch locks the prosthetic knee joint;
      the latch is configured to automatically and purely mechanically disengage from the notch to unlock the prosthetic knee joint in response to the ground reaction force being anterior to the virtual lock axis, thereby permitting the prosthetic knee joint to pivot; and
      the latch is configured to automatically return to an engaging position in response to the pivot of the prosthetic knee joint.

2. A prosthetic knee according to claim 1, further comprising an early stance flexion module comprising an early stance flexion joint configured to pivot about an early stance flexion axis, distinct from the knee joint pivot axis and the virtual lock axis, and pivotally couple the upper leg to the prosthetic knee joint about the early stance flexion axis, wherein position of the early stance flexion axis is adjustable, relative to position of the knee joint pivot axis, and torsional stiffness of the early stance flexion joint is adjustable.

3. A prosthetic knee according to claim 2, wherein the early stance flexion module is configured to apply an adjustable preload torque that must be overcome to pivot the early stance flexion joint about the early stance flexion axis.

4. A prosthetic knee according to claim 1, further comprising a hydraulic damper coupled to dampen the pivot of the prosthetic knee joint about the knee joint pivot axis and configured to provide at least 1.1 times as much damping during flexion of the prosthetic knee joint as during extension of the prosthetic knee joint.

5. A prosthetic knee according to claim 4, wherein the hydraulic damper comprises a linear hydraulic damper comprising a piston and at least one one-way valve.

6. A prosthetic knee according to claim 4, wherein the hydraulic damper comprises a first rotary hydraulic damper mechanically coupled via a first one-way clutch to the prosthetic knee joint and a second rotary hydraulic damper mechanically coupled to the prosthetic knee joint.

7. A prosthetic knee according to claim 6, wherein the second rotary hydraulic damper mechanically is coupled to the prosthetic knee joint via a second one-way clutch, wherein the first and second one-way clutches are configured to rotate in opposite directions.

8. A prosthetic knee according to claim 6, wherein each rotary hydraulic damper of the first and second rotary hydraulic dampers comprises:
   a cylinder having an inner wall, the inner wall defining a volume;
   an axle longitudinally disposed within the cylinder for rotation therewithin, relative to the cylinder;
   a rotor mechanically coupled to the axle for rotation therewith, the rotor having an outer surface spaced apart from the inner wall; and
   a hydraulic fluid disposed within a volume defined between the inner wall and the outer surface.

9. A prosthetic knee according to claim 6, wherein each rotary hydraulic damper of the first and second rotary hydraulic dampers comprises:
   a housing;
   an axle longitudinally disposed within the housing for rotation therewithin, relative to the housing;
   a plurality of longitudinally spaced apart first plates mechanically coupled to the axle for rotation therewith;
   a plurality of second plates rigidly coupled to the housing and interdigitated with the plurality of longitudinally spaced apart first plates so as to define respective volumes between adjacent pairs of first and second plates, and collectively defining a total inter-plate volume; and
   a hydraulic fluid disposed within the total inter-plate volume.

10. A prosthetic knee according to claim 4, wherein the hydraulic damper comprises a first rotary hydraulic damper and a second rotary hydraulic damper, at least one of the first and second rotary hydraulic dampers comprising a directionally-dependent rotary hydraulic damper comprising:
    a cylinder having an inner wall, the inner wall defining a volume;
    a hydraulic fluid disposed within the volume;
    an axle longitudinally disposed within the cylinder for rotation therewithin, relative to the cylinder;
    at least one fin spaced apart from the inner wall and mechanically coupled to the axle by a spring for rotation with the axle, the fin and the spring being configured to deflect the spring in response to a shear force of the hydraulic fluid, between the fin and the inner wall, as a result of rotation of the axle in a first direction, and thereby increase spacing between the fin and the inner wall; and a stop configured to at least limit deflection of the spring when the axle rotates in a direction opposite the first direction.

11. A prosthetic knee according to claim 10, wherein each fin of the at least one fin comprises a portion, less than all, of a cylinder and is disposed parallel to the inner wall.

12. A prosthetic knee according to claim 1, wherein the linkage is a four-bar linkage comprising a ground link, two grounded links, a floating link and four rotating joints, wherein the ground link is configured to mechanically couple to the lower leg and the floating link is mechanically coupled to the prosthetic knee joint and the latch, such that the latch pivots about the virtual lock axis as a result of pivoting of the two grounded links about two respective rotating joints of the four rotating joints.

13. A prosthetic knee according to claim 12, wherein positions of at least two rotating joints of the four rotating joints are adjustable to alter position of the virtual lock axis.

14. A prosthetic knee according to claim 1, further comprising a swing extension energy storage module comprising a third spring configured to deflect in response to pivoting of the prosthetic knee joint, such that the third spring is deflected when the first notch is engaged by the hook, and when deflected, the third spring urges the prosthetic knee joint to pivot about the knee joint pivot axis so as to increase knee flexion angle of the prosthetic knee joint.

15. A prosthetic knee according to claim 1, wherein the latch is configured to automatically engage when the prosthetic knee joint returns to an angle of between about 0° and about 1° of knee flexion.

16. A prosthetic knee according to claim 1, wherein the latch is configured to automatically engage at at least two distinct points, such that when the latch is engaged at a second of the at least two distinct points the prosthetic knee joint is bent at an angle of between about 1° and about 15° of knee flexion, and when the latch is engaged at a first of the at least two distinct points the prosthetic knee joint is bent at an angle of between about 0° and about 1° of knee flexion.

17. A prosthetic knee according to claim 16, wherein the latch defines a second notch that is engagable by the hook such that, when the hook is engaged in the first notch, the latch is engaged at the first of the at least two distinct points, and when the hook is engaged in the second notch, the latch is engaged at the second of the at least two distinct points.

18. A prosthetic knee according to claim 1, wherein the virtual lock axis is disposed along an imaginary line extending through the knee joint pivot axis and a ground reaction force transition point, wherein the ground reaction force transition point corresponds to a location of the center of pressure when the prosthetic knee initiates late stance flexion.

19. A prosthetic knee according to claim 18, wherein the foot has a length, and the ground reaction force transition point is located between: (a) about 5% of the length of the foot from a toe of the foot and (b) about 5% of the length of the foot from a heel of the foot.

20. A prosthetic knee according to claim 18, wherein the virtual lock axis is disposed a distance about $r=\theta/s$ from the knee joint pivot axis along the imaginary line, wherein s equals a distance the latch moves to disengage and $\theta$ is less than about 1°.

* * * * *